(12) United States Patent
Chun et al.

(10) Patent No.: US 9,662,000 B2
(45) Date of Patent: May 30, 2017

(54) VISUALIZATION APPARATUS AND SYSTEM FOR ENHANCED HAND-EYE COORDINATION

(71) Applicant: Hankookin, LLC, Raleigh, NC (US)

(72) Inventors: James Jiwen Chun, Raleigh, NC (US); Andrew Youngho Chun, Raleigh, NC (US); Angela Soyoung Chun, Raleigh, NC (US); Jennifer Miseong Chun, Raleigh, NC (US)

(73) Assignee: HANKOOKIN, INC., Raleigh, NC (US)

( * ) Notice: Subject to any disclaimer, the term of this patent is extended or adjusted under 35 U.S.C. 154(b) by 837 days.

(21) Appl. No.: 14/013,026

(22) Filed: Aug. 28, 2013

(65) Prior Publication Data
US 2015/0064643 A1  Mar. 5, 2015

(51) Int. Cl.
| *A61C 1/00* | (2006.01) |
| *A61B 1/247* | (2006.01) |
| *A61B 1/00* | (2006.01) |

(52) U.S. Cl.
CPC ............ *A61B 1/247* (2013.01); *A61B 1/0005* (2013.01); *A61B 1/00009* (2013.01); *A61B 1/00016* (2013.01); *A61B 1/00045* (2013.01)

(58) Field of Classification Search
CPC ..... A61C 19/004; A61B 1/247; A61B 1/0013; A61B 1/00045; A61B 1/00–1/00062
USPC .................................................. 433/29, 215
See application file for complete search history.

(56) References Cited

U.S. PATENT DOCUMENTS

| 4,786,154 | A | 11/1988 | Fantone et al. | |
| 6,276,934 | B1* | 8/2001 | Rakocz | A61B 1/0669 433/29 |
| 6,761,561 | B2* | 7/2004 | Mandelkern | A61B 1/00016 433/29 |
| 8,186,997 | B2* | 5/2012 | Binner | A61C 17/221 128/898 |
| 2008/0160477 | A1* | 7/2008 | Stookey | A61B 1/00041 433/31 |
| 2010/0030031 | A1 | 2/2010 | Goldfarb et al. | |
| 2011/0183283 | A1* | 7/2011 | Strassl | A61C 1/0046 433/31 |
| 2015/0141793 | A1 | 5/2015 | Hong et al. | |

* cited by examiner

*Primary Examiner* — Yogesh Patel
(74) *Attorney, Agent, or Firm* — Ash Tankha; Lipton, Weinberger & Husick

(57) ABSTRACT

A visualization apparatus and a system for enhancing hand-eye coordination during a medical procedure are provided. The visualization apparatus includes an elongate support member, a head member, an operating head element, and a processor. The head member connected to the elongate support member at a predetermined angle includes an angled wall for mounting a reflector. The operating head element connected to an upper end of the head member mounts and supports an objective lens. The objective lens focuses light from an operating field to a reflector to create an image of the operating field. An eyepiece lens accommodated in the elongate support member or the head member magnifies the created image. The processor operatively communicating with an image receiver processes and transmits the magnified image to a viewer. The orientation of the magnified image on the viewer is similar to the orientation of the operating field, thereby enhancing hand-eye coordination.

19 Claims, 16 Drawing Sheets

VISUALIZATION APPARATUS AND SYSTEM FOR ENHANCED HAND-EYE COORDINATION

BACKGROUND

As a person's eyes views an object in a three dimensional (3D) space, the person's brain moves his/her hands in the same 3D space in response to the object viewed, for example, in a vertical dimension, a horizontal dimension, and a transverse dimension. While viewing a mirror image of a three-dimensional (3D) space, the visual observation is altered, that is, the orientation of the 3D space is reversed. The vertical dimension and the transverse dimension remain the same, but the horizontal dimension is altered. There is typically a left-right flip over of about 180 degrees. In such a situation, the brain is confused and is not able to function properly. Although the visual observation is reversed while viewing the mirror image, the brain still guides the hands by moving the hands towards the right when the hands are in fact moving towards the left and vice versa. The brain has to be trained to guide the hands to move in the 3D space with reference to the mirror image. However, as day to day activities are carried out in a normal space, the brain is confused as to when to switch between the two different spaces, for example, between the real image of the 3D space and the mirror image of the 3D space.

In many medical and dental procedures, the eye cannot directly view an operating field. During a dental procedure, a dentist normally uses a hand mirror to view the operating field. For example, during a root canal treatment, the position of a root canal is inside an oral cavity, and the only visual is provided through the reflection of the hand mirror. As the reflection in the hand mirror is an altered image, the brain is not able to guide the hands accurately in the proper direction. Moreover, dentists have to rely solely on their tactile sensation and cannot resort to the precision of visual guidance. Hence, in order to let the brain function normally, there is a need for a visualization apparatus that provides a normal vision of the operating field by creating an image having the same orientation as that of the operating field.

Furthermore, medical practitioners, for example, dentists have to bend their heads to observe an image reflected by the hand mirror. During a long procedure, bending the head for a long period tends to create tremendous stress in the neck area and in the brain. Medical practitioners, for example, dental professionals are therefore known to have a high morbidity rate. In order to reduce mental and physical labor during such medical procedures, there is a need for a visualization apparatus that provides a direct 3D vision of the operating field without the need for a user of the visualization apparatus to bend his/her head, to provide enhanced hand-eye coordination and eliminate stress on the neck, back, and brain of the user.

Hand-eye coordination refers to a coordinated control of hand movement with eye movement and processing of visual information to guide reaching and grasping actions to execute a task. In many medical and dental surgeries, hand-eye coordination is an important factor affecting the performance of medical practitioners during the surgeries. During most dental surgeries, a proper vision of the operating field is unavailable due to limited access to the operating field. For example, during a root canal treatment, visualization of a tooth pulpal chamber is difficult due to the position of the tooth, the small opening of the pulpal chamber, the tiny and sometimes invisible orifice of the root canal, poor lightning into the pulpal chamber, etc. Without proper instrumentation, detailed viewing of a pulpal space is not possible and the root canal treatment must be performed without visual guidance.

Recent advances in visualization of digital information have enabled a higher level of hand-eye coordination during a complicated surgery such as a root canal surgery. Large microscopes, for example, the Seiler microscope are commonly used by medical practitioners, for example, endodontists, to gain vision into the pulpal space. Although the large microscopes have a high magnification power, the large microscopes can only be used at a distance from the tooth, and operate only if a direct visual is available from a distance. A common tool that allows a high level of hand-eye coordination is, for example, a high speed dental handpiece. With moderate training, dentists use the high speed dental handpiece to remove decay and reshape a tooth surface. The dental handpiece resembles a writing pen with an operating angle that allows fine motion control. Therefore, there is a need for a visualization apparatus configured as a dental handpiece of a predetermined small size that can be inserted in the operating field, for example, the oral cavity for visualizing the pulpal chamber to achieve enhanced hand-eye coordination.

Hence, there is a long felt but unresolved need for a method, a visualization apparatus, and a system that enhances hand-eye coordination during a medical procedure without requiring a user of the visualization apparatus to bend his/her head. Moreover, there is a need for a visualization apparatus that resembles a handpiece and is small enough to be inserted in the operating field. Furthermore, there is a need for a visualization apparatus that provides a direct vision of the operating field by creating an image having the same orientation as that of the operating field.

SUMMARY OF THE INVENTION

This summary is provided to introduce a selection of concepts in a simplified form that are further disclosed in the detailed description of the invention. This summary is not intended to identify key or essential inventive concepts of the claimed subject matter, nor is it intended for determining the scope of the claimed subject matter.

The method, the visualization apparatus, and the system disclosed herein address the above stated needs for enhancing hand-eye coordination during a medical procedure without requiring a user of the visualization apparatus to bend his/her head. The visualization apparatus disclosed herein resembles a handpiece and is small enough to be inserted in an operating field. As used herein, the term "operating field" refers to a specific area of a patient's body where a medical procedure, for example, a surgery is performed. The operating field comprises areas immediately surrounding and directly involved in the specific area where the medical procedure is performed. The visualization apparatus disclosed herein provides a direct vision of the operating field by creating an image having the same orientation as that of the operating field.

The visualization apparatus disclosed herein is a microscope resembling a handpiece such as a dental handpiece. The visualization apparatus disclosed herein comprises an elongate support member, a head member, an operating head element, and at least one processor. The elongate support member allows maneuvering of the visualization apparatus within the operating field. In an embodiment, the elongate support member defines an axial hollow space for accommodating an eyepiece lens. In an embodiment, the elongate support member comprises an elongate handle and a neck element. The elongate handle defines a first axial hollow space for accommodating an image receiver and the processor. In another embodiment, the eyepiece lens is accommodated in the first axial hollow space of the elongate handle. The neck element is operably connected to and extends axially from an upper end of the elongate handle. In an embodiment, the neck element defines a second axial hollow space for accommodating the eyepiece lens.

The head member is operably connected to an upper end of the elongate support member at a predetermined angle with respect to the elongate support member. In an embodiment, the head member is rigidly connected to the upper end of the elongate support member at the predetermined angle with respect to the elongate support member. The head member at the predetermined angle enhances accessibility to an operating field and enhances motion control, for example, position, movement, and velocity control of the visualization apparatus within the operating field during a medical procedure. The head member comprises an angled wall for mounting a reflector along an inner surface of the angled wall. In an embodiment, the head member defines a hollow space in fluid communication with the axial hollow space defined within the elongate support member for accommodating the eyepiece lens.

The operating head element is operably connected to an upper end of the head member. The operating head element mounts and supports an objective lens. The objective lens is in optical communication with the reflector and the eyepiece lens. The reflector and the eyepiece lens are optically aligned with a focal point of the objective lens. The objective lens focuses light from the operating field to the reflector to create an image of the operating field during the medical procedure. The reflector redirects the created image to the eyepiece lens to enable the eyepiece lens to magnify the created image. The eyepiece lens accommodated in the elongate support member or the head member, in optical communication with the reflector, magnifies the created image.

The processor of the visualization apparatus is operably positioned within the axial hollow space defined within the elongate support member. The processor is in operative communication with the image receiver. The image receiver is positioned within the axial hollow space defined within the elongate support member and proximal to the eyepiece lens for receiving the magnified image from the eyepiece lens. The image receiver transmits the magnified image to the processor. The processor processes and transmits the magnified image to a viewer for visualization of the operating field during the medical procedure. In an embodiment, the viewer is an electronic device, for example, a computer, a laptop, a tablet computing device, an image capture device, a display unit, any other suitable computing equipment, etc., configured for visualizing the operating field based on the magnified image transmitted by the processor. In another embodiment, the viewer is a viewing device, for example, a wearable computer with a head mounted display such as the Google Glass® of Google Inc. In another embodiment, the viewer is the eyes of a user, for example, a dentist who is performing a dental procedure. The visualization apparatus disclosed herein ensures that the orientation of the magnified image on the viewer is substantially similar to the orientation of the operating field, thereby enhancing hand-eye coordination during the medical procedure. The viewer displays the magnified image in an orientation substantially similar to the orientation of the operating field.

In an embodiment, the visualization apparatus further comprises multiple light sources, for example, light emitting diodes mounted proximal to and surrounding the objective lens on the operating head element. The light sources illuminate the operating field during the medical procedure. In an embodiment, the visualization apparatus further comprises an adjustable member operably connected to a frame configured to support the eyepiece lens within the elongate support member or the head member to adjust a position of the eyepiece lens with respect to the objective lens for adjusting focus of the objective lens. In another embodiment, the visualization apparatus further comprises an adjustable member operably connected to a frame configured to support the image receiver within the axial hollow space of the elongate support member to adjust a position of the image receiver with respect to the eyepiece lens for facilitating reception of the magnified image by the image receiver. In an embodiment, the visualization apparatus further comprises an orientation indicator embedded in the elongate support member or the head member. The orientation indicator records an instantaneous position and an instantaneous orientation of the visualization apparatus on creation of the image of the operating field and transmits the recorded position and orientation of the visualization apparatus to the processor of the visualization apparatus. The processor corrects the orientation of the magnified image based on the recorded position and orientation of the visualization apparatus to a preset orientation.

Disclosed herein are also a system and a method for enhancing hand-eye coordination during a medical procedure. The system disclosed herein comprises the visualization apparatus, the viewer, one or more command sensors, and a control system. The viewer is operably connected to the visualization apparatus and configured to display the magnified image on a graphical user interface provided by the viewer in an orientation substantially similar to an orientation of the operating field, thereby enhancing hand-eye coordination during the medical procedure. The control system is operably connected to the visualization apparatus. In an embodiment, the control system is installed in the viewer. In another embodiment, the control system is externally connected to the viewer, for example, via a wired network or a wireless network. The control system is also operably connected to one or more command sensors, for example, microphones. The control system is connected to the command sensors, for example, via a network, for example, a wired network, a wireless network, a communication network that implements Bluetooth® of Bluetooth Sig, Inc, etc. The command sensors detect user commands in one or more modes, for example, an audio mode, a video mode, a text mode, an audiovisual mode, a multimedia mode, etc., and any combination thereof. As used herein, the term "user commands" refers to commands issued by a user, for example, a dentist for performing an action. The user commands are, for example, audio commands, voice commands, textual commands, video commands, etc. The command sensors transmit the detected user commands to the control system. The control system comprises a voice activated command software executable by at least one processor. The voice activated command software defines instructions for recognizing the user commands transmitted by the command sensors. The voice activated command software defines instructions for execution of the user commands by the processor of the control system. The voice activated command software transmits the instructions for the execution of the user commands to the processor of the control system. The processor of the control system, on receiving the execution instructions from the voice activated command software, processes the user commands and converts the user commands into executable commands. The processor of the control system transmits the converted user commands to the visualization apparatus via a network, for example, a wired network, a wireless network, etc. The processor of the visualization apparatus receives the transmitted user commands and processes the transmitted user commands to perform one or more actions on the visualization apparatus. The actions are, for example, adjusting a position of the eyepiece lens of the visualization apparatus for adjusting focus of the objective lens of the visualization apparatus, changing the orientation of the magnified image for enhanced visualization of the operating field, etc.

In an embodiment, the system disclosed herein further comprises an image recognition application executable by at least one processor, installed in the viewer. The image recognition application recognizes the orientation of the magnified image created by the visualization apparatus. The image recognition application also corrects the orientation of the magnified image to match the orientation of the operating field.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and components disclosed herein.

DETAILED DESCRIPTION OF THE INVENTION

Figure 1A:
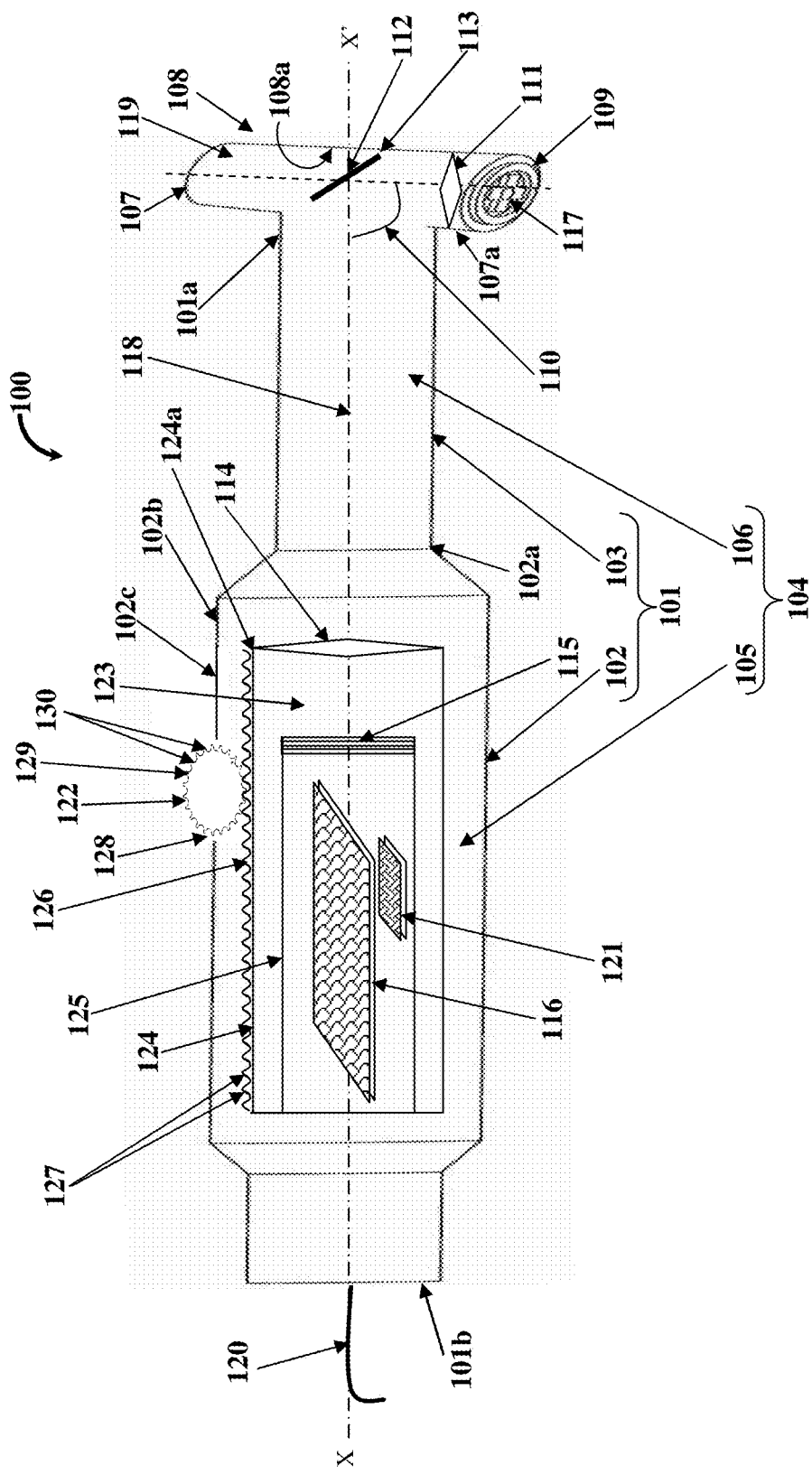
FIGS. 1A-1B exemplarily illustrate partial cutaway views of a visualization apparatus for enhancing hand-eye coordination during a medical procedure.
Figure 1B:
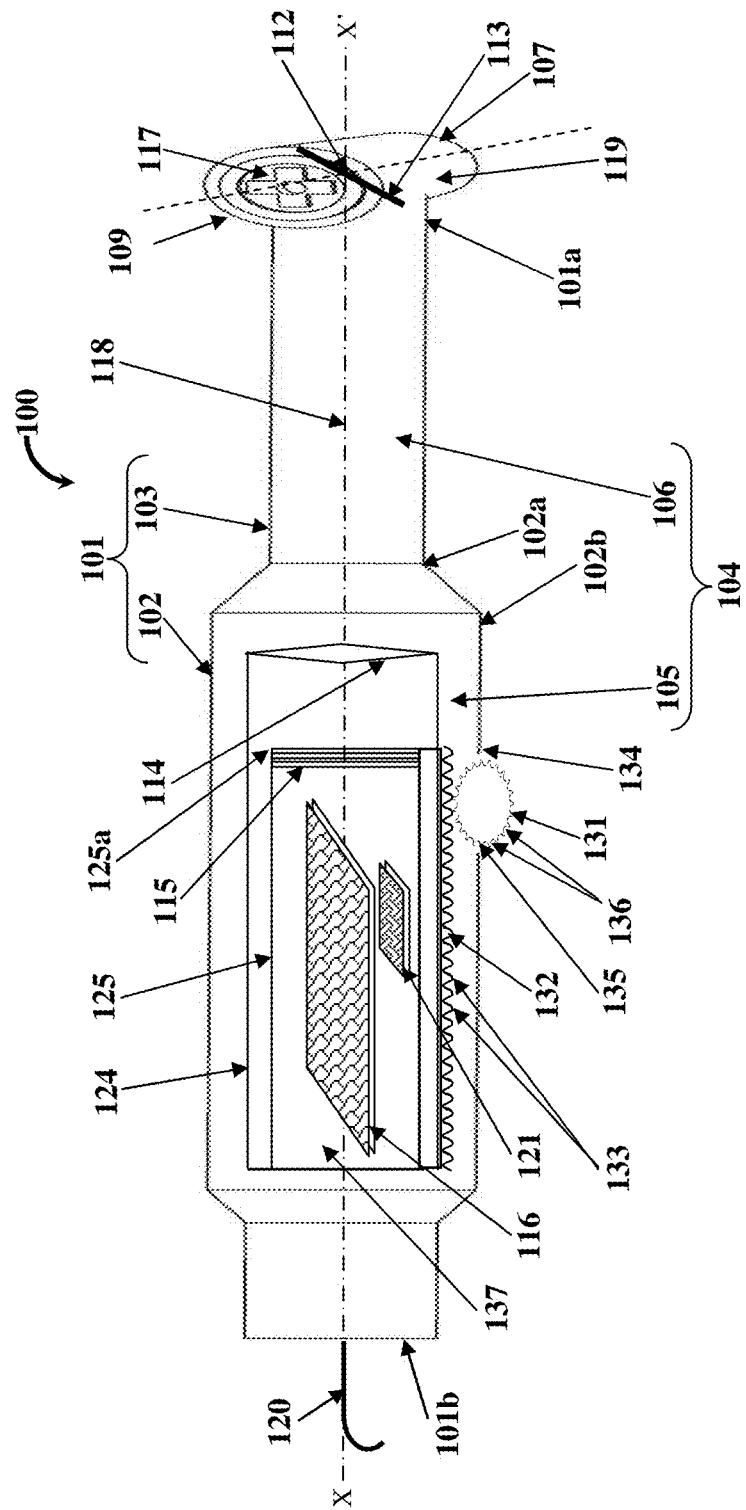
Figure 2A:
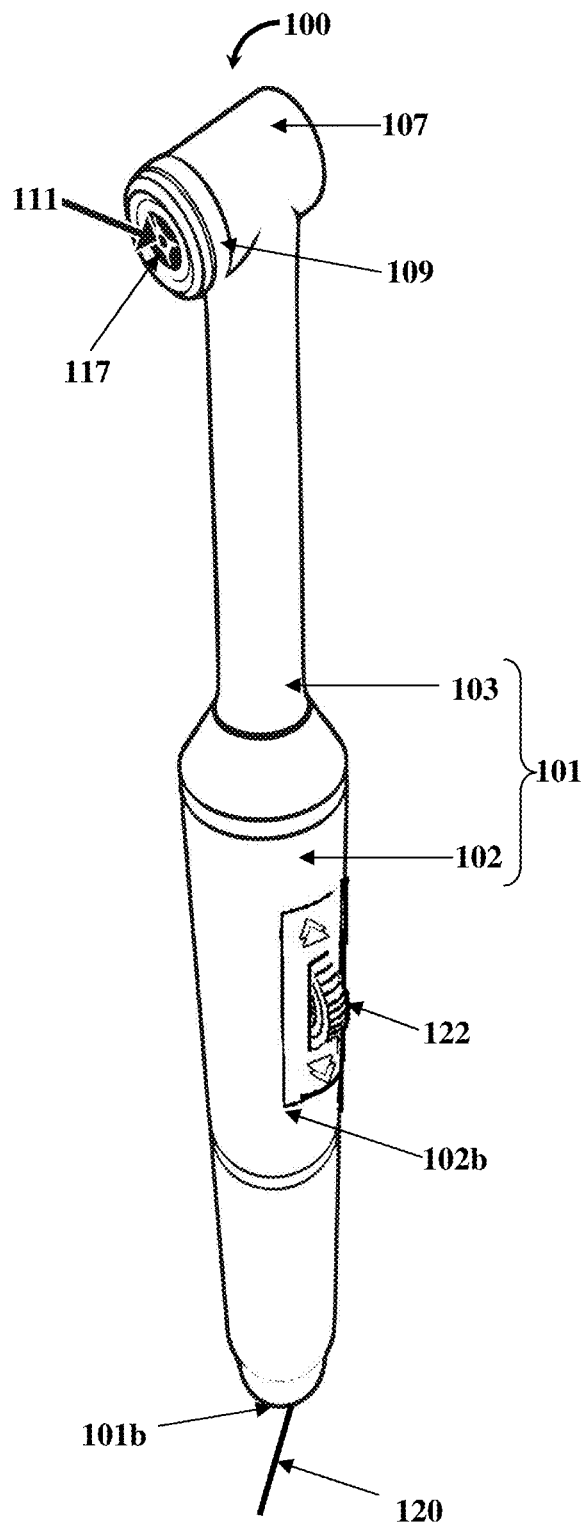
FIG. 2A exemplarily illustrates an isometric view of the visualization apparatus.
Figure 2B:
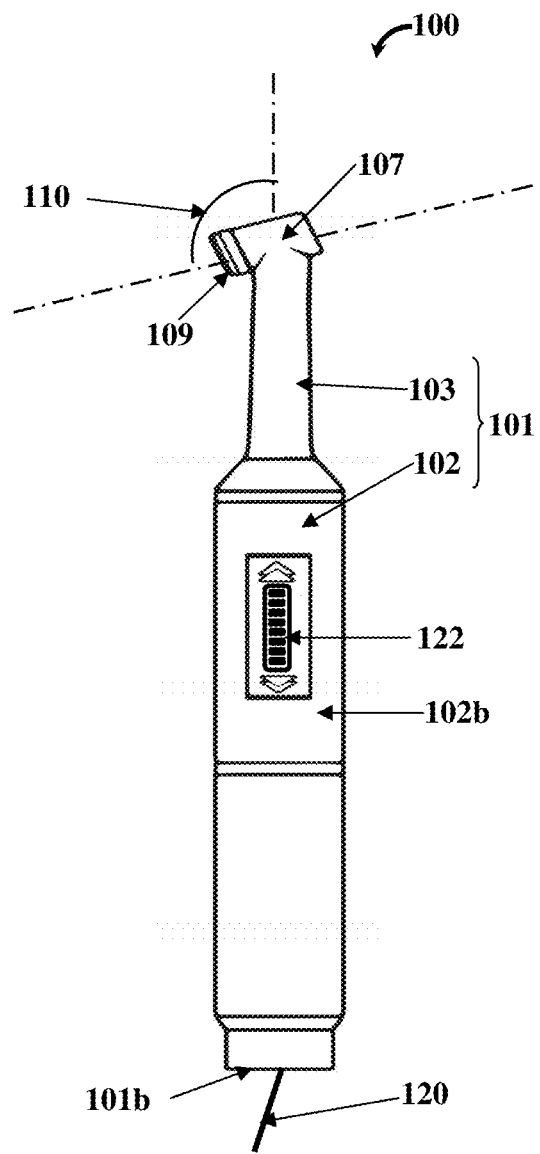
FIG. 2B exemplarily illustrates a side elevation view of the visualization apparatus.
Figure 2C:
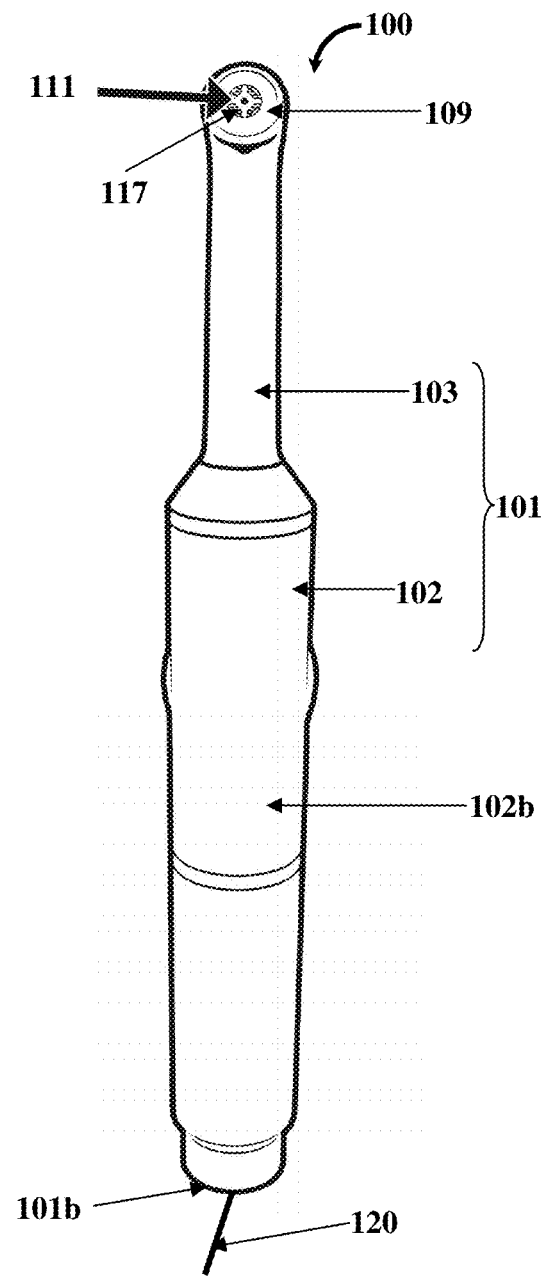
FIG. 2C exemplarily illustrates a front perspective view of the visualization apparatus.
Figure 2D:
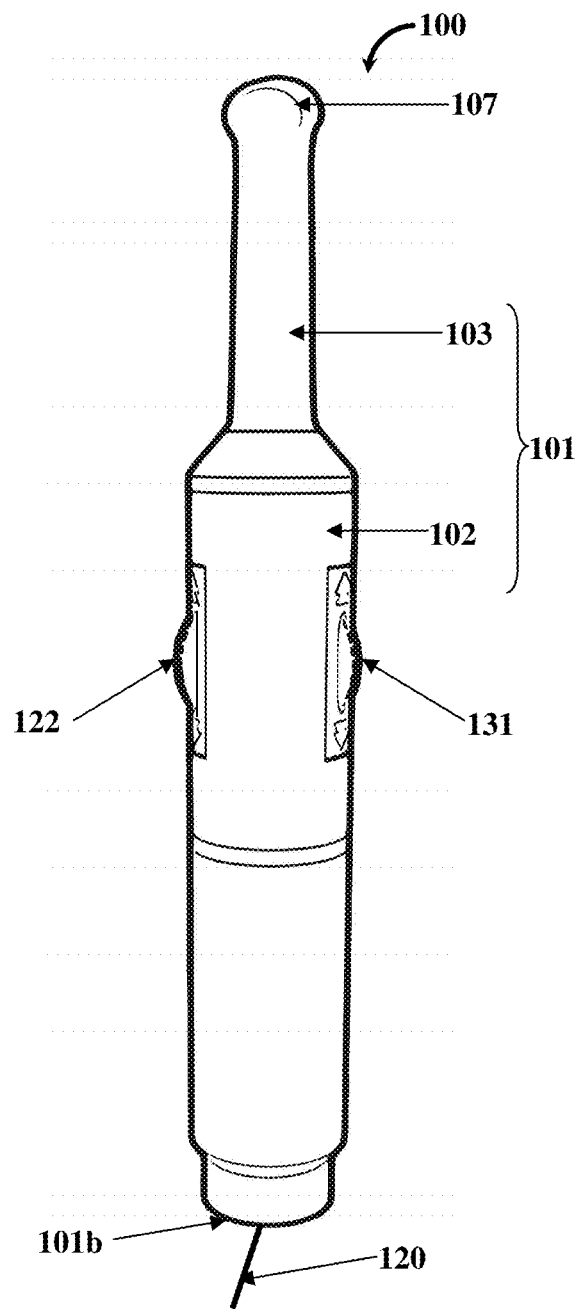
FIG. 2D exemplarily illustrates a rear perspective view of the visualization apparatus.

FIGS. 1A-1B exemplarily illustrate partial cutaway views of a visualization apparatus 100 for enhancing hand-eye coordination during a medical procedure. Partial opposing halves of the visualization apparatus 100 are exemplarily illustrated in FIGS. 1A-1B. The visualization apparatus 100 disclosed herein is implemented, for example, as a small sized microscope with an angled head member 107. The visualization apparatus 100 has a high magnification power.

Figure 6A:
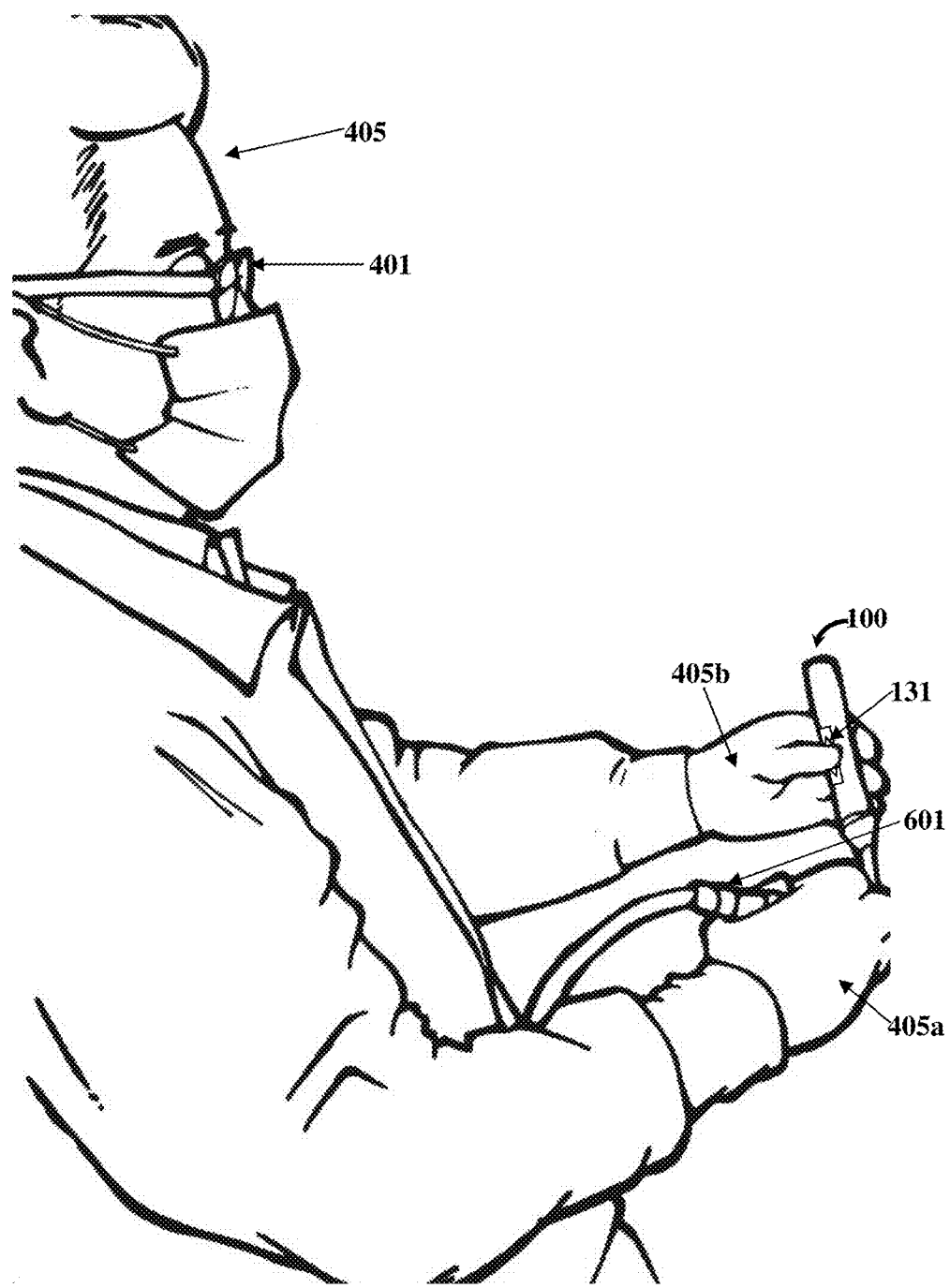
FIGS. 6A-6E exemplarily illustrate an implementation of the visualization apparatus during a medical procedure.

The magnification power is, for example, within a range of 10× to 100×. The visualization apparatus 100 disclosed herein enhances hand-eye coordination and provides and follows a direct vision at any angle and space in a small operating field 604 exemplarily illustrated in FIGS. 6D-6E. As used herein, the term "operating field" refers to a specific area of a patient's body where a medical procedure, for example, a surgery is performed. The operating field comprises areas immediately surrounding and directly involved in the specific area where the medical procedure is performed. The operating field is, for example, a pulpal chamber of a tooth during a root canal treatment. The visualization apparatus 100 is configured as a high speed hand tool, for example, a handpiece. The small size of the visualization apparatus 100 and the resemblance to a handpiece allow better control of a medical practitioner's hand and eye coordination during a medical procedure, for example, a surgery. The visualization apparatus 100 can be used, for example, by neural surgeons operating on fine nerve tissue in small and difficult to access spaces.

The visualization apparatus 100 disclosed herein comprises an elongate support member 101, a head member 107, an operating head element 109, and at least one processor 116. The elongate support member 101 allows maneuvering of the visualization apparatus 100 within an operating field, for example, in difficult to access spaces in a patient's oral cavity. In an embodiment, the elongate support member 101 defines an axial hollow space 104 for accommodating an eyepiece lens 114 as exemplarily illustrated in FIG. 1A. In another embodiment, the eyepiece lens 114 is accommodated within a hollow space 119 defined in the head member 107. In an embodiment, the elongate support member 101 comprises an elongate handle 102 and a neck element 103. The elongate handle 102 defines an axial hollow space 105 for accommodating, for example, an image receiver 115 and the processor 116. The neck element 103 is operably connected to and axially extends from an upper end 102a of the elongate handle 102. In an embodiment, the neck element 103 defines an axial hollow space 106 for accommodating the eyepiece lens 114. In another embodiment, the eyepiece lens 114 is accommodated in the axial hollow space 105 of the elongate handle 102 as exemplarily illustrated in FIGS. 1A-1B. Although the detailed description refers to the image receiver 115 and the processor 116 being positioned in the axial hollow space 105 of the elongate handle 102, the image receiver 115 and the processor 116 may be positioned at any location within the visualization apparatus 100 to allow them to operably communicate with each other for enhancing hand-eye coordination during a medical procedure.

The head member 107 of the visualization apparatus 100 is operably connected to an upper end 101a of the elongate support member 101. In an embodiment, the head member 107 is rigidly connected to the upper end 101a of the elongate support member 101 at a predetermined angle 110 with respect to an axis X-X' 118 of the elongate support member 101. The predetermined angle 110 is, for example, within a range of about 100° to about 110°. For example, the head member 107 is rigidly connected to the upper end 101a of the elongate support member 101 at 105° with respect to the axis X-X' 118 of the elongate support member 101. In another embodiment, the head member 107 is rotatably connected to the upper end 101a of the elongate support member 101 at a predetermined angle 110. In this embodiment, the predetermined angle 110 can be changed and adjusted with respect to the axis X-X' 118 of the elongate support member 101. In an embodiment, the head member 107 is mounted on the elongate support member 101 by a universal fitting that allows the head member 107 to be rotated in the X direction, the Y direction, or the Z direction, and thereafter rigidly positioned at any angle with respect to the elongate support member 101, for example, by a nut and screw arrangement. The head member 107 at the predetermined angle 110 enhances accessibility to an operating field. The head member 107 also enhances motion control of the visualization apparatus 100 within the operating field during a medical procedure, for example, a surgery, a dental procedure, etc. The head member 107 allows a user, for example, a dentist to easily maneuver the visualization apparatus 100 in a limited access area such as the oral cavity, and hence provides an enhanced motion control such as position, movement and velocity control of the visualization apparatus 100 within the operating field during the medical procedure. As used herein, the term "user" refers to a medical practitioner, for example, a dentist, a neural surgeon, etc., who uses the visualization apparatus 100 for visualizing an operating field. In an embodiment, the head member 107 defines a hollow space 119 in fluid communication with the axial hollow space 104 defined within the elongate support member 101, for accommodating the eyepiece lens 114. The head member 107 comprises an angled wall 108 for mounting a reflector 113, for example, a reflective mirror or a prism along an inner surface 108a of the angled wall 108.

The operating head element 109 is operably connected to an upper end 107a of the head member 107. In an embodiment, the operating head element 109 is rigidly connected to the upper end 107a of the head member 107. The operating head element 109 mounts and supports an objective lens 111. The objective lens 111 is in optical communication with the reflector 113 and the eyepiece lens 114. The objective lens 111 focuses light from the operating field to the reflector 113. The reflector 113 is optically aligned with a focal point 112 of the objective lens 111. The objective lens 111 collects light from the operating field and brings the light to focus for creating an image of the operating field during the medical procedure. The reflector 113 redirects the created image to the eyepiece lens 114. The eyepiece lens 114 is optically aligned with the focal point 112 of the objective lens 111. The reflector 113 redirects the created image to the eyepiece lens 114 to enable the eyepiece lens 114 to magnify the created image. The eyepiece lens 114 in optical communication with the reflector 113 magnifies the created image. In an embodiment, the visualization apparatus 100 further comprises multiple light sources 117, for example, light emitting diodes mounted proximal to and surrounding the objective lens 111 on the operating head element 109. The light sources 117 illuminate the operating field during the medical procedure.

The processor 116 of the visualization apparatus 100 is operably positioned within the axial hollow space 104 defined within the elongate support member 101. As used herein, the term "processor" refers to any one or more microprocessors, central processing unit (CPU) devices, finite state machines, computers, microcontrollers, digital signal processors, logic, a logic device, an electronic circuit, an application specific integrated circuit (ASIC), a field-programmable gate array (FPGA), a chip, etc., or any combination thereof, capable of executing computer programs or a series of commands, instructions, or state transitions, or may also be implemented as a processor set comprising, for example, a general purpose microprocessor and a math or graphics co-processor. The processor 116 is in operative communication with the image receiver 115. The image receiver 115 is positioned within the axial hollow space 104 of the elongate support member 101 and proximal to the eyepiece lens 114 for receiving the magnified image from the eyepiece lens 114. The processor 116 processes and transmits the magnified image to a viewer 401 exemplarily illustrated in FIGS. 4A-4B and FIG. 6A, for visualization of the operating field during the medical procedure. In an embodiment, the viewer 401 is an electronic device, for example, a computer, a laptop, a portable computing device, a tablet computing device, an image capture device, a display unit, any other suitable computing equipment, etc., configured for visualizing the operating field based on the magnified image transmitted by the processor 116. In another embodiment, the viewer 401 is a viewing device or a vision device, for example, a wearable computer with a head mounted display such as the Google Glass® of Google Inc. The processor 116 transmits the magnified image to the viewer 401 via a network, for example, a wired network, a wireless network, etc. In another embodiment, the viewer 401 is the eyes of a user, for example, a dentist who is performing a dental procedure. A visual of the operating field can be obtained by the user without the need for the user to bend his/her neck or back. The visual is provided to the user on a display screen of the viewer 401, for example, an eye glass such as the Google Glass®. The visualization apparatus 100 disclosed herein ensures that the orientation of the magnified image on the viewer 401 is substantially similar to the orientation of the operating field comprising, for example, a target object, thereby enhancing hand-eye coordination during the medical procedure.

In an embodiment, the visualization apparatus 100 further comprises adjustable members 122 and 131 extending partially outwards from openings 128 and 134, respectively, for example, a rectangular opening, an oval opening, a circular opening, etc., defined on an outer wall 102b of the elongate handle 102 of the elongate support member 101, and extending partially inwards via the openings 128 and 134 inside the axial hollow space 105 of the elongate handle 102 of the elongate support member 101. The adjustable member 122 exemplarily illustrated in FIG. 1A is operably connected or engaged to a frame 124 configured to support the eyepiece lens 114, for example, within the axial hollow space 105 of the elongate handle 102 of the elongate support member 101. In an embodiment, the frame 124 is configured as a hollow cylindrical tube accommodated within the axial hollow space 105 of the elongate handle 102 of the elongate support member 101. The eyepiece lens 114 is removably attached to a distal end 124a of the frame 124 exemplarily illustrated in FIG. 1A. In an embodiment, the frame 124 defines an axial hollow space 123 configured to accommodate another frame 125 as exemplarily illustrated in FIG. 1A. The adjustable member 122 adjusts a position of the eyepiece lens 114 with respect to the objective lens 111 for adjusting focus of the objective lens 111. A cutaway view of the visualization apparatus 100, showing the operating head element 109 oriented in a downward direction and the adjustable member 122 configured to rollably move the eyepiece lens 114 for enhancing hand-eye coordination during a medical procedure is exemplarily illustrated in FIG. 1A.

In an embodiment, the adjustable member 122 is functionally configured as a roller shaped wheel that rotates in a clockwise direction and a counterclockwise direction for rollably moving the eyepiece lens 114 with respect to the objective lens 111. The adjustable member 122 is engageably connected to a rack gear 126 configured on the frame 124. The rack gear 126 is a linear gear rail with a teeth portion 127 configured to rollably engage with a teeth portion 130 of a pinion gear 129 configured on the adjustable member 122 to translate a rotational motion of the adjustable member 122 to a reciprocatory linear motion of the frame 124. Rotational motion applied to the adjustable member 122 causes the frame 124 to move, thereby translating the rotational motion of the adjustable member 122 to a linear motion of the frame 124. The adjustable member 122 enables movement of the eyepiece lens 114 fixedly attached to the distal end 124a of the frame 124 within the axial hollow space 104 defined within the elongate support member 101 as exemplarily illustrated in FIG. 1A.

The adjustable member 131 exemplarily illustrated in FIG. 1B is operably connected or engaged to the frame 125 configured to support the image receiver 115, for example, within the axial hollow space 105 of the elongate handle 102 of the elongate support member 101. In an embodiment, the frame 125 is configured as a hollow cylindrical tube accommodated within the axial hollow space 123 of the frame 124 exemplarily illustrated in FIG. 1A. The image receiver 115 is removably attached to a distal end 125a of the frame 125. In an embodiment, the frame 125 defines an axial hollow space 137 configured to accommodate the processor 116 and an orientation indicator 121 exemplarily illustrated in FIGS. 1A-1B. The adjustable member 131 adjusts a position of the image receiver 115 with respect to the eyepiece lens 114 for facilitating the reception of the magnified image by the image receiver 115. A cutaway view of the visualization apparatus 100, showing the operating head element 109 oriented in an upward direction and the adjustable member 131 configured to rollably move the image receiver 115 for enhancing hand-eye coordination during a medical procedure is exemplarily illustrated in FIG. 1B.

In an embodiment, the adjustable member 131 is functionally configured as a roller shaped wheel that rotates in a clockwise direction and a counterclockwise direction for rollably moving the image receiver 115 with respect to the eyepiece lens 114. In an embodiment, the adjustable member 131 is engageably connected to a rack gear 132 configured on the frame 125. The rack gear 132 is a linear gear rail with a teeth portion 133 configured to rollably engage with a teeth portion 136 of a pinion gear 135 configured on the adjustable member 131 to translate a rotational motion of the adjustable member 131 to a reciprocatory linear motion of the frame 125. Rotational motion applied to the adjustable member 131 causes the frame 125 to move, thereby translating the rotational motion of the adjustable member 131 to a linear motion of the frame 125. The rack gear 132 extends outwardly from the frame 124 through an opening track (not shown) defined along the frame 124. The opening track on the frame 124 enables the adjustable member 131 to engageably connect to the rack gear 132 configured on the frame 125. The adjustable member 131 enables movement of the image receiver 115 fixedly attached to the distal end 125a of the frame 125 within the axial hollow space 104 defined within the elongate support member 101 as exemplarily illustrated in FIG. 1B.

The adjustable members 122 and 131 positioned at a predetermined distance from each other are rollably connected to the rack gears 126 and 132, respectively, fixedly connected to the frames 124 and 125, respectively. The adjustable members 122 and 131 move bidirectionally. The user, for example, a dentist focuses the image by moving the eyepiece lens 114 nearer or further from the objective lens 111 by rolling the adjustable member 122 in a clockwise direction or a counterclockwise direction. The user further adjusts the reception of the magnified image by the image receiver 115 by moving the image receiver 115 nearer or further from the eyepiece lens 114 by rolling the adjustable member 131 in a clockwise direction or a counterclockwise direction. When the user rolls the adjustable member 122 in the clockwise direction or the counterclockwise direction, the rack gear 126 rollably connected to the adjustable member 122 moves in a reciprocatory direction, thereby linearly moving the eyepiece lens 114 fixedly connected to the frame 124 away from or nearer to the objective lens 111, respectively. Furthermore, when the user rolls the adjustable member 131 in a clockwise direction or a counterclockwise direction, the rack gear 132 rollably connected to the adjustable member 131 moves in a reciprocatory direction, thereby linearly moving the image receiver 115 operably connected to the frame 125 away from or nearer to the eyepiece lens 114.

Although the detailed description refers to rack and pinion arrangements for adjusting the position of the eyepiece lens 114 with respect to the objective lens 111 and for adjusting the position of the image receiver 115 with respect to the eyepiece lens 114, the scope of the visualization apparatus 100 and the method disclosed herein is not limited to adjustments using rack and pinion arrangements, but may be extended to include other functionally equivalent structures and methods for adjusting the position of the eyepiece lens 114 with respect to the objective lens 111 and for adjusting the position of the image receiver 115 with respect to the eyepiece lens 114.

In an embodiment, the visualization apparatus 100 further comprises an orientation indicator 121 embedded in the elongate support member 101 as exemplarily illustrated in FIGS. 1A-1B, or in the head member 107. The orientation indicator 121 corrects the orientation of the magnified image to match the orientation of the operating field comprising, for example, a target object during the medical procedure. The orientation indicator 121 is configured, for example, as a motion and position sensor that detects instantaneous motion, position, and orientation of the visualization apparatus 100, and transmits information about the detected motion, position, and orientation of the visualization apparatus 100 to the processor 116. The orientation indicator 121 records an instantaneous three-dimensional position and an instantaneous orientation of the visualization apparatus 100 on creation of the image of the operating field. Each image comprises the position and orientation of the visualization apparatus 100. In an embodiment, the orientation indicator 121 records instantaneous two-dimensional or instantaneous multi-dimensional position and orientation of the visualization apparatus 100 on creation of the image of the operating field. The orientation indicator 121 transmits the recorded position and orientation of the visualization apparatus 100 to the processor 116. The processor 116 corrects the orientation of the magnified image by aligning each created image based on the recorded position and orientation of the visualization apparatus 100 as exemplarily illustrated in FIG. 5B. In an embodiment, the visualization apparatus 100 creates a series of images of the target object at multiple positions and orientations. The visualization apparatus 100 stores and transmits the series of images to the viewer 401, a control system 402 exemplarily illustrated in FIGS. 4A-4B, or another computer system for construction of three dimensional images of the target object.

In an embodiment, the visualization apparatus 100 comprises one or more supplementary objective lenses (not shown) mounted and supported on the operating head element 109 at multiple angles. The supplementary objective lenses create images of the operating field at the angles simultaneously for construction of one or more composite images of the operating field. As used herein, the term "composite images" refers to images constructed using a combination of multiple images captured at multiple angles and positions with respect to a target object. The composite images are, for example, two-dimensional images, three-dimensional images, etc. At the beginning of a medical procedure, the user sets a first position and a first observation orientation for the visualization apparatus 100 to create a first image of the target object. The images subsequently created by the visualization apparatus 100 are displayed on the viewer 401 according to the set observation orientation, irrespective of the subsequent orientation angles of the visualization apparatus 100, as exemplarily illustrated in FIG. 5B. The images of the operating field are transmitted to the processor 116. In an embodiment, the processor 116 processes the images of the operating field, constructs one or more composite images from the processed images, and transmits the constructed composite images to the viewer 401. The viewer 401 displays the composite images of the operating field to the user during the medical procedure. In an embodiment, the processor 116 processes and transmits the images of the operating field, for example, to a control system 402 or another computer system for construction of the composite images.

FIGS. 2A-2D exemplarily illustrate an isometric view, a side elevation view, a front perspective view, and a rear perspective view, respectively, of the visualization apparatus 100. The visualization apparatus 100 resembles a handpiece, for example, a dental handpiece in size and shape. The visualization apparatus 100 disclosed herein comprises the elongate support member 101 having the elongate handle 102 and the neck element 103, an angled head member 107 with the operating head element 109, and the light sources 117 as disclosed in the detailed description of FIGS. 1A-1B. The visualization apparatus 100 disclosed herein further comprises the adjustment members 122 and 131 fixedly connected to the outer wall 102b of the elongate handle 102 of the elongate support member 101 as disclosed in the detailed description of FIGS. 1A-1B.

In an embodiment, the visualization apparatus 100 further comprises a wire connection element 120 extending from the lower end 101b of the elongate support member 101. One end of the wire connection element 120 is operably connected to the processor 116 exemplarily illustrated in FIGS. 1A-1B, within the visualization apparatus 100, while the other end of the wire connection element 120 that extends outwardly from the lower end 101b of the elongate support member 101 can be connected to the viewer 401 exemplarily illustrated in FIGS. 4A-4B and FIG. 6A or another computing device, control system 402, or computer system. The processor 116 transmits a magnified image of an operating field to the viewer 401 via the wired connection element 120.

Figure 3:
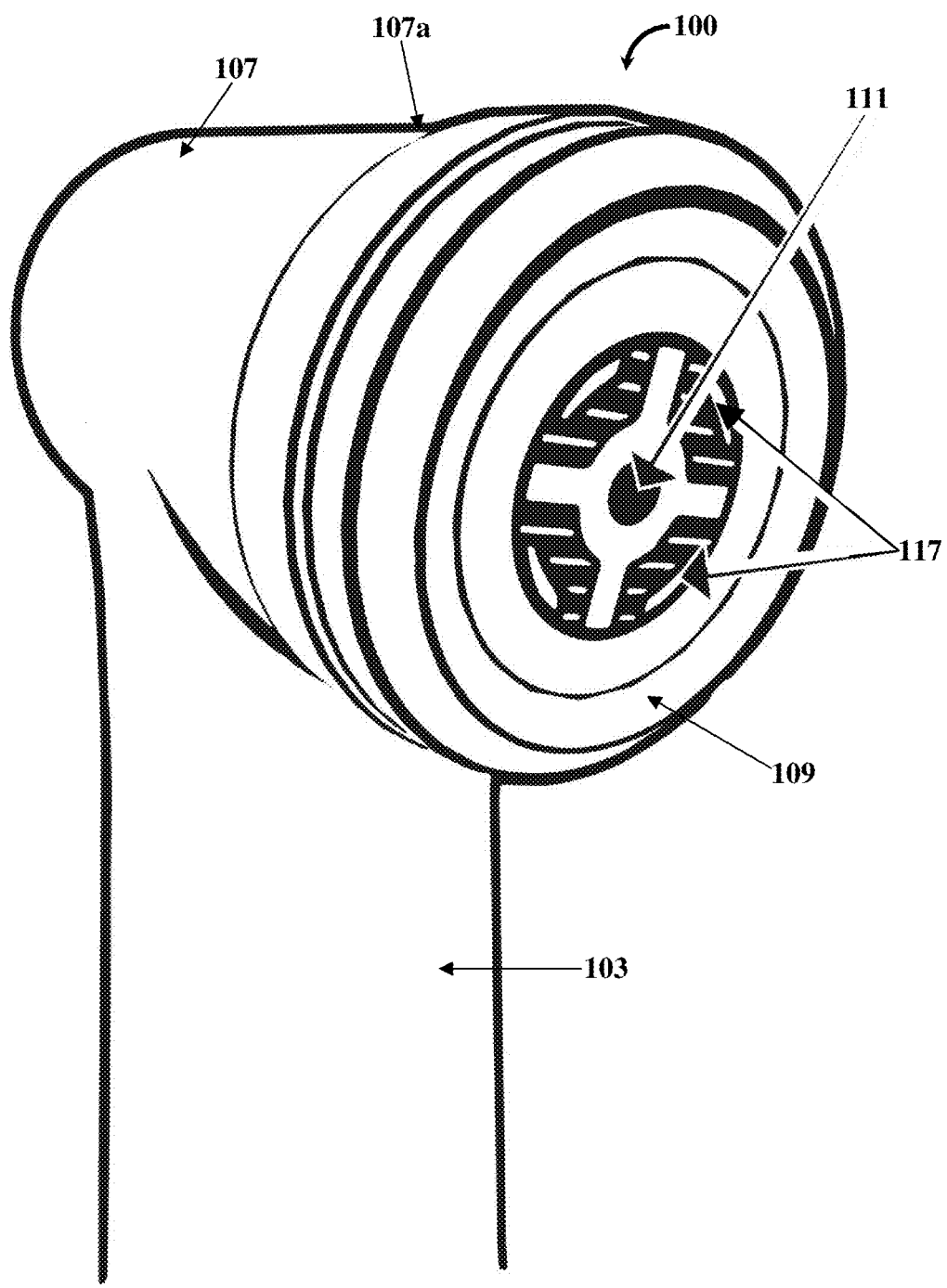
FIG. 3 exemplarily illustrates an enlarged partial perspective view of the visualization apparatus, showing an angled head member of the visualization apparatus.

FIG. 3 exemplarily illustrates an enlarged partial perspective view of the visualization apparatus 100, showing an angled head member 107. The operating head element 109 is rigidly connected to the upper end 107a of the angled head member 107. The operating head element 109 mounts and supports the objective lens 111 and multiple light sources 117 as exemplarily illustrated in FIG. 3. The light sources 117, for example, light emitting diodes are mounted proximal to and surrounding the objective lens 111 on the operating head element 109 for illuminating an operating field during the medical procedure as disclosed in the detailed description of FIGS. 1A-1B.

Figure 4A:
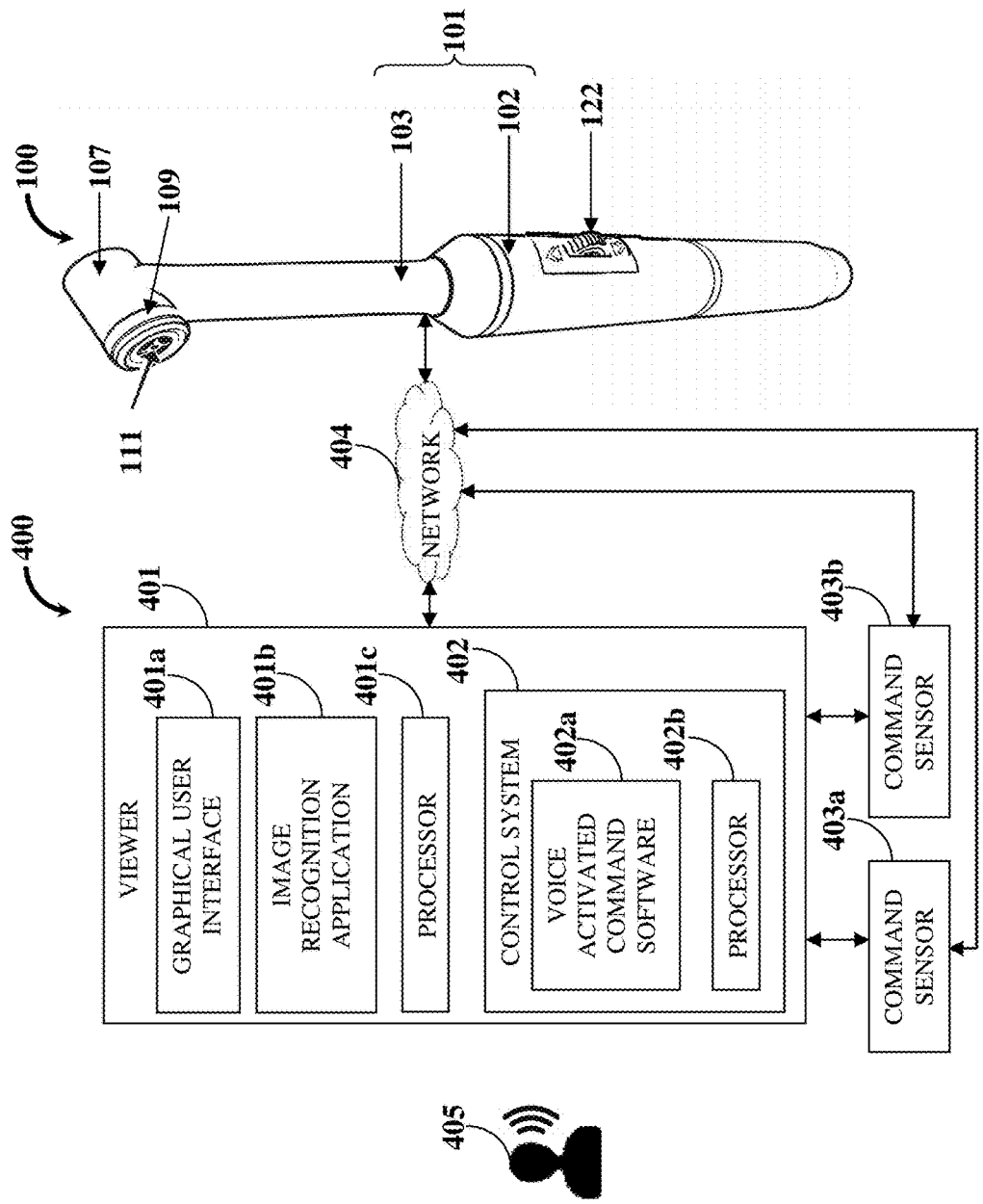
FIGS. 4A-4B exemplarily illustrate implementations of a system for enhancing hand-eye coordination during a medical procedure.
Figure 4B:
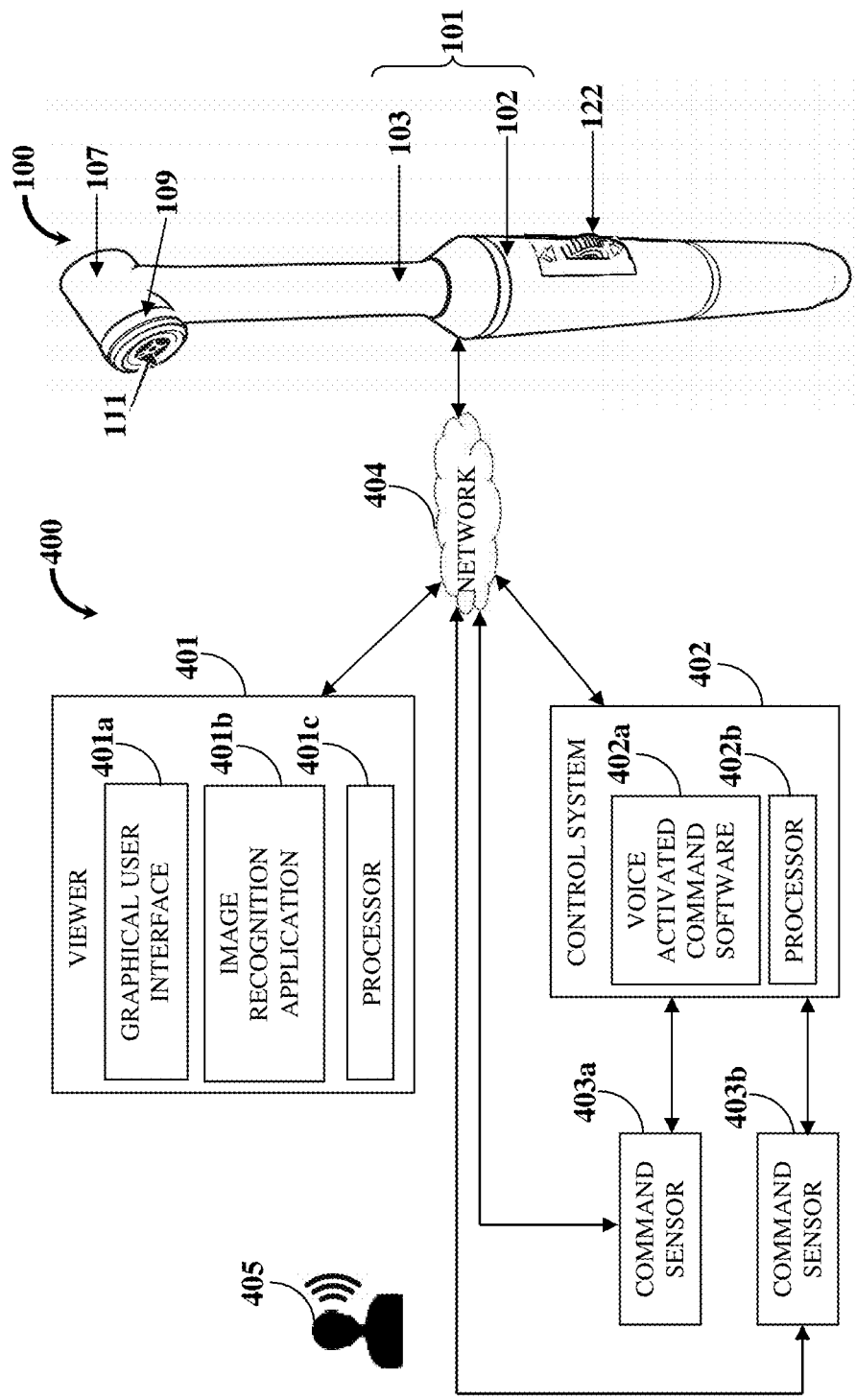

FIGS. 4A-4B exemplarily illustrate implementations of a system 400 for enhancing hand-eye coordination during a medical procedure. The system 400 disclosed herein comprises the visualization apparatus 100 and the viewer 401. The visualization apparatus 100 comprises the elongate support member 101 having the elongate handle 102 and the neck element 103, the head member 107, the operating head element 109, the objective lens 111, the orientation indicator 121, and the adjustable members 122 and 131 as disclosed in the detailed description of FIGS. 1A-1B. The visualization apparatus 100 creates an image of an operating field and magnifies the created image as disclosed in the detailed description of FIGS. 1A-1B. The processor 116 of the visualization apparatus 100 exemplarily illustrated in FIGS. 1A-1B processes the magnified image and transmits the magnified image to the viewer 401 for visualization of the operating field. The viewer 401 is operably connected to the visualization apparatus 100 via a network 404, for example, a wireless network, a wired network, a communication network that implements Bluetooth® of Bluetooth Sig, Inc, etc. The viewer 401 displays the magnified image on a graphical user interface 401a provided by the viewer 401 in an orientation substantially similar to the orientation of the operating field, thereby enhancing hand-eye coordination during the medical procedure.

The system 400 disclosed herein further comprises a control system 402 and one or more command sensors 403a, 403b, etc. The control system 402 is operably connected to the viewer 401 and the visualization apparatus 100. In an embodiment, the control system 402 is installed in the viewer 401 as exemplarily illustrated in FIG. 4A. In another embodiment, the control system 402 is externally connected to the viewer 401 and the visualization apparatus 100 via the network 404 as exemplarily illustrated in FIG. 4B. In an embodiment, the control system 402 is embedded in an external computing device. The computing device is an electronic device, for example, a personal computer, a tablet computing device, a mobile computer, a portable computing device, a laptop, a touch centric device, an image capture device, a workstation, a portable electronic device, a network enabled computing device, an interactive network enabled communication device, any other suitable computing equipment, and combinations of multiple pieces of computing equipment, etc.

In an embodiment, the control system 402 comprises a processor 402b and a voice activated command software 402a executable by the processor 402b installed in the control system 402. The viewer 401 is in operative communication with the voice activated command software 402a. The command sensors 403a, 403b, etc., for example, microphones are operably connected to the control system 402 directly or via the network 404. In an embodiment, the command sensors 403a, 403b, etc., communicate with the control system 402 in the viewer 401 directly or via the network 404 as exemplarily illustrated in FIG. 4A. In another embodiment, the command sensors 403a, 403b, etc., communicate with the control system 402 externally connected to the viewer 401 directly or via the network 404 as exemplarily illustrated in FIG. 4B. The command sensors 403a, 403b, etc., detect user commands in one or more modes, for example, an audio mode, a video mode, a text mode, an audiovisual mode, a multimedia mode, etc., and any combination thereof, and transmit the user commands to the control system 402. As used herein, the term "user commands" refers to commands issued by a user 405, for example, a dentist for performing an action. The user commands comprise, for example, audio commands, voice commands, textual commands, video commands, etc.

The voice activated command software 402a in the control system 402 is programmed to recognize certain words as user commands received from the command sensors 403a, 403b, etc. Upon receiving confirmation on correct interpretation of the user commands from the user 405, the voice activated command software 402a defines instructions for execution of the user commands and transmits the instructions for the execution of the user commands to the processor 402b of the control system 402. The processor 402b, on receiving the execution instructions from the voice activated command software 402a, proceeds with the execution of the user commands. The processor 402b executes the instructions defined by the voice activated command software 402a to process the user commands and converts the user commands into executable commands. The processor 402b transmits the converted user commands to the visualization apparatus 100. The processor 116 of the visualization apparatus 100 receives the transmitted user commands and processes the converted user commands for performing one or more actions on the visualization apparatus 100. The actions performed by the visualization apparatus 100 are, for example, adjusting the position of the eyepiece lens 114 of the visualization apparatus 100 for adjusting focus of the objective lens 111 of the visualization apparatus 100, changing the orientation of the magnified image for enhanced visualization of the operating field, etc.

In an embodiment, the system 400 disclosed herein further comprises an image recognition application 401b installed in the viewer 401. The image recognition application 401b is executable by at least one processor 401c of the viewer 401 for recognizing the orientation of the magnified image created by the visualization apparatus 100 and for correcting the orientation of the magnified image to match the orientation of the operating field.

The processors 116, 401c, 402b, etc., of the system 400 disclosed herein are selected, for example, from the Intel® processors such as the Itanium® microprocessor or the Pentium® processors, Advanced Micro Devices (AMD®) processors such as the Athlon® processor, UltraSPARC® processors, microSPARC™ processors, Hp® processors, International Business Machines (IBM®) processors such as the PowerPC® microprocessor, the MIPS® reduced instruction set computer (RISC) processor of MIPS Technologies, Inc., RISC based computer processors of ARM Holdings, Motorola® processors, etc. The processors 116, 401c, 402b, etc., execute operating systems selected, for example, from the Linux® operating system, the Unix® operating system, any version of the Microsoft® Windows® operating system, the Mac OS of Apple Inc., the IBM® OS/2, VxWorks® of Wind River Systems, inc., QNX Neutrino® developed by QNX Software Systems Ltd., the Palm OS®, the Solaris operating system developed by Sun Microsystems, Inc., the Android operating system, the Windows Phone™ operating system of Microsoft Corporation, the BlackBerry® operating system of Research in Motion Limited, the iOS operating system of Apple Inc., the Symbian® operating system of Symbian Foundation Limited, etc. The voice activated command software 402a and the image recognition application 401b are stored on non-transitory computer readable storage mediums, for example, memory units (not shown) communicatively coupled to the processors 402b and 401c of the control system 402 and the viewer 401 respectively. As used herein, the term "non-transitory computer readable storage medium" refers to all computer readable media, for example, non-volatile media such as optical discs or magnetic disks, volatile media such as a register memory, a processor cache, etc., and transmission media such as wires that constitute a system bus coupled to the processors, for example, 402b and 401c, except for a transitory, propagating signal.

Figure 5A:
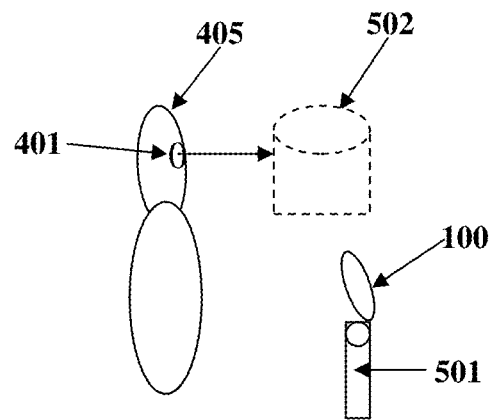
FIGS. 5A-5B exemplarily illustrate the orientation of a magnified image of a target object in an operating field captured by the visualization apparatus for multiple orientations of the visualization apparatus.
Figure 5B:
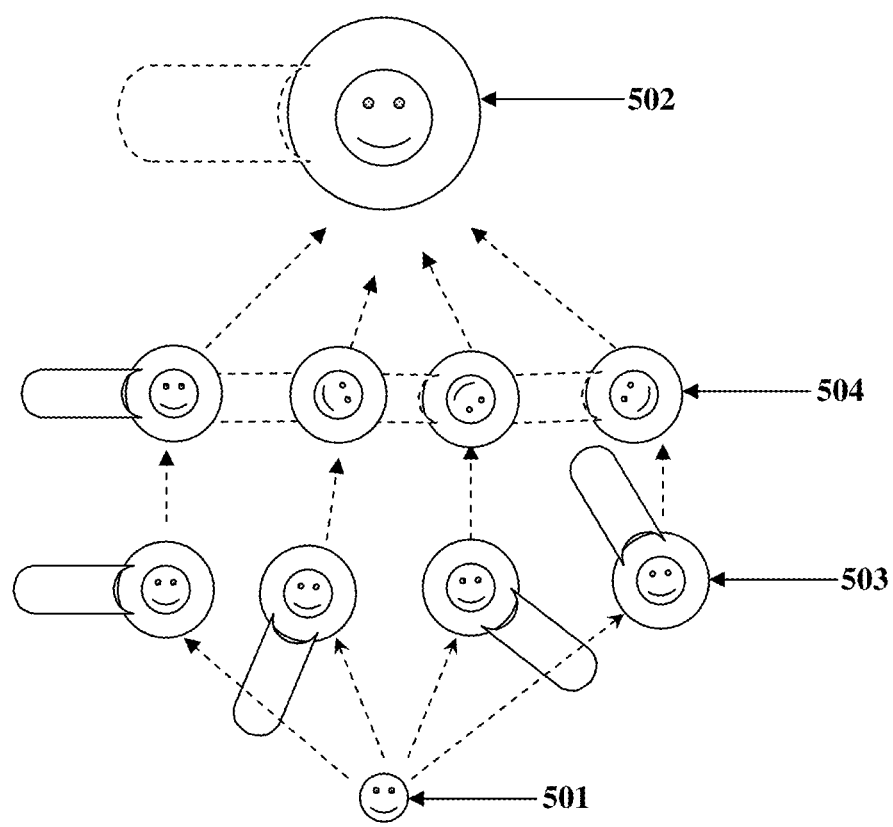

FIGS. 5A-5B exemplarily illustrate the orientation of a magnified image 502 of a target object 501 in an operating field captured by the visualization apparatus 100 exemplarily illustrated in FIGS. 1A-1B and FIGS. 2A-2D, for multiple orientations of the visualization apparatus 100. When a user 405 uses the visualization apparatus 100 to view an operating field, the visualization apparatus 100 displays the magnified image 502 of a target object 501 on the viewer 401 exemplarily illustrated in FIGS. 4A-4B and FIG. 6A, in an orientation substantially similar to the orientation of the target object 501 as exemplarily illustrated in FIG. 5A. The user 405 does not have to bend his/her head to view the magnified image 502 on the viewer 401. Since the visualization apparatus 100 renders the operating field in a direct vision, the user 405 can coordinate hand movements and complete the medical procedure faster and more accurately. The visualization apparatus 100 renders the magnified image 502 to the viewer 401 in the same orientation even though the user 405 positions, moves, or rotates the visualization apparatus 100 in and around the operating field, as and when desired by the user 405 as exemplarily illustrated in FIG. 5B.

FIG. 5B exemplarily illustrates the target object 501 in the operating field, different orientations 503 of the visualization apparatus 100, the images captured 504 by the visualization apparatus 100 at different orientations, and the magnified image 502 of the target object 501 in the operating field rendered to the viewer 401. As exemplarily illustrated in FIG. 5B, the magnified image 502 displayed on the viewer 401 has the same orientation as that of the operating field. While performing a medical procedure, the user 405 positions the visualization apparatus 100 in multiple orientations 503. The visualization apparatus 100 captures the images 504 of the operating field at different orientations of the visualization apparatus 100. The visualization apparatus 100 then orients all the images in the different orientations to create a magnified image 502 whose orientation matches the orientation of the operating field. In an embodiment, the visualization apparatus 100 allows the user 405 to choose and fix a comfortable orientation of the operating field before starting the medical procedure. Although the visualization apparatus 100 can be moved and rotated, the magnified image 502 displayed on the viewer 401 remains in the same image orientation as exemplarily illustrated in FIG. 5B.

In an embodiment, the image recognition application 401b of the viewer 401 exemplarily illustrated in FIGS. 4A-4B recognizes each new magnified image 502 and the orientation of the magnified image 502. The image recognition application 401b orients the images captured 504 at the multiple orientations to the original orientation chosen by the user 405. The image recognition application 401b presents the magnified image 502 to the user 405 via the viewer 401 in the same orientation fixed by the user 405 irrespective of the manner in which the visualization apparatus 100 is held by the user 405. The orientation of the magnified image 502 remains the same throughout the medical procedure as exemplarily illustrated in FIG. 5B, and the user 405 does not need to think for adjusting the orientation to guide the hand movement of the user 405.

The orientation indicator 121 embedded in the elongate support member 101 or the head member 107 of the visualization apparatus 100 corrects the orientation of the magnified image 502 captured by the visualization apparatus 100 as the visualization apparatus 100 changes position. The orientation indicator 121 corrects the orientation of the magnified image 502 to the original orientation determined by the user 405.

FIGS. 6A-6E exemplarily illustrate an implementation of the visualization apparatus 100 during a medical procedure such as a dental procedure. As the visualization apparatus 100 resembles a handpiece, the visualization apparatus 100 can be held by the user 405, for example, a dentist while performing the medical procedure as exemplarily illustrated in FIG. 6A and FIGS. 6C-6E. Consider an example where the user 405 wears a viewer 401, for example, a Google Glass® over his/her eyes and holds a medical instrument, for example, a dental instrument such as a dental handpiece 601 in one hand 405a as exemplarily illustrated in FIG. 6A, while holding the visualization apparatus 100 in the other hand 405b in an operating field 604 in a patient's oral cavity, while performing the medical procedure as exemplarily illustrated in FIGS. 6D-6E. The visualization apparatus 100 can be positioned in the operating field 604 at any position and at any suitable observation orientation as required by the user 405 while performing the medical procedure. The visualization apparatus 100 can be positioned in the operating field 604 in a direction opposite to the direction of the dental handpiece 601 as exemplarily illustrated in FIG. 6D. The visualization apparatus 100 can also be positioned closer to the dental handpiece 601 as exemplarily illustrated in FIG. 6E.

Figure 6B:
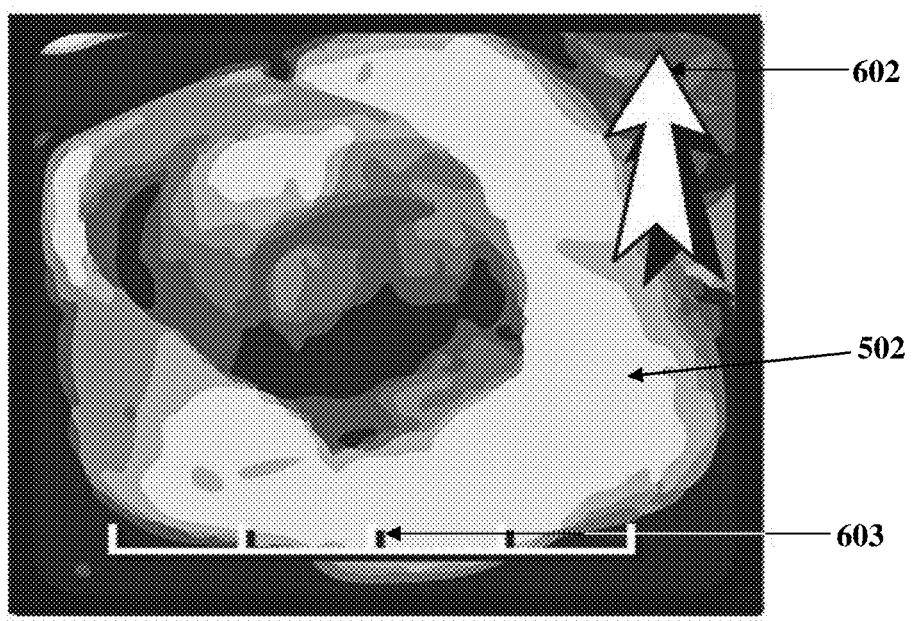
Figure 6C:
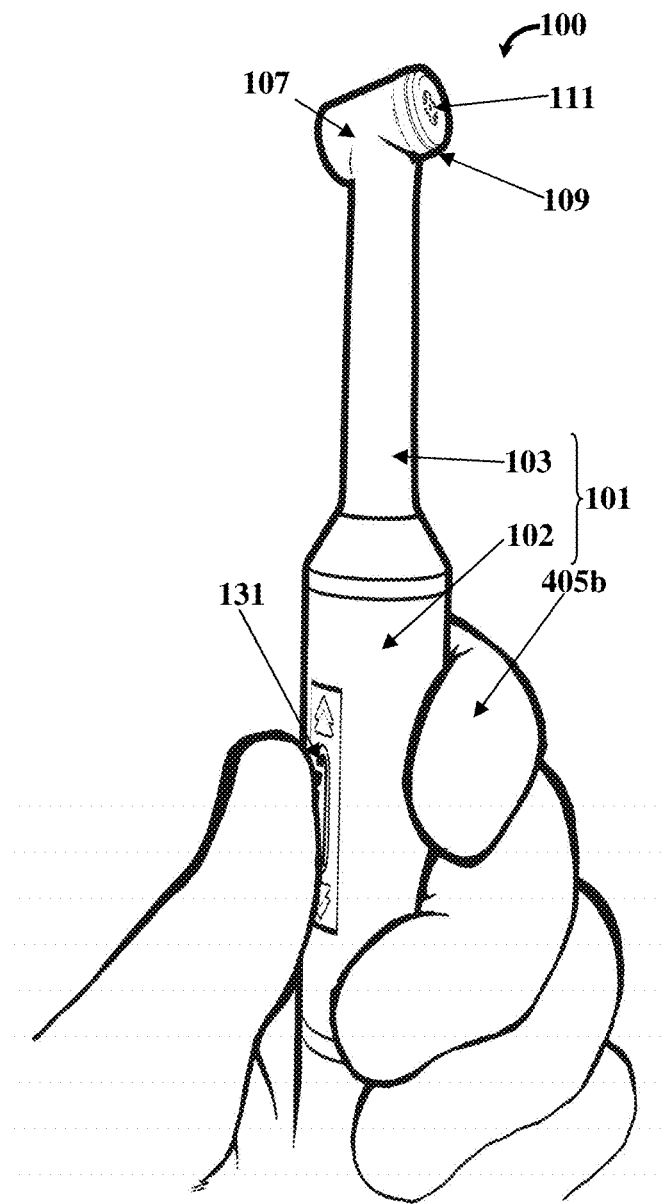
Figure 6D:
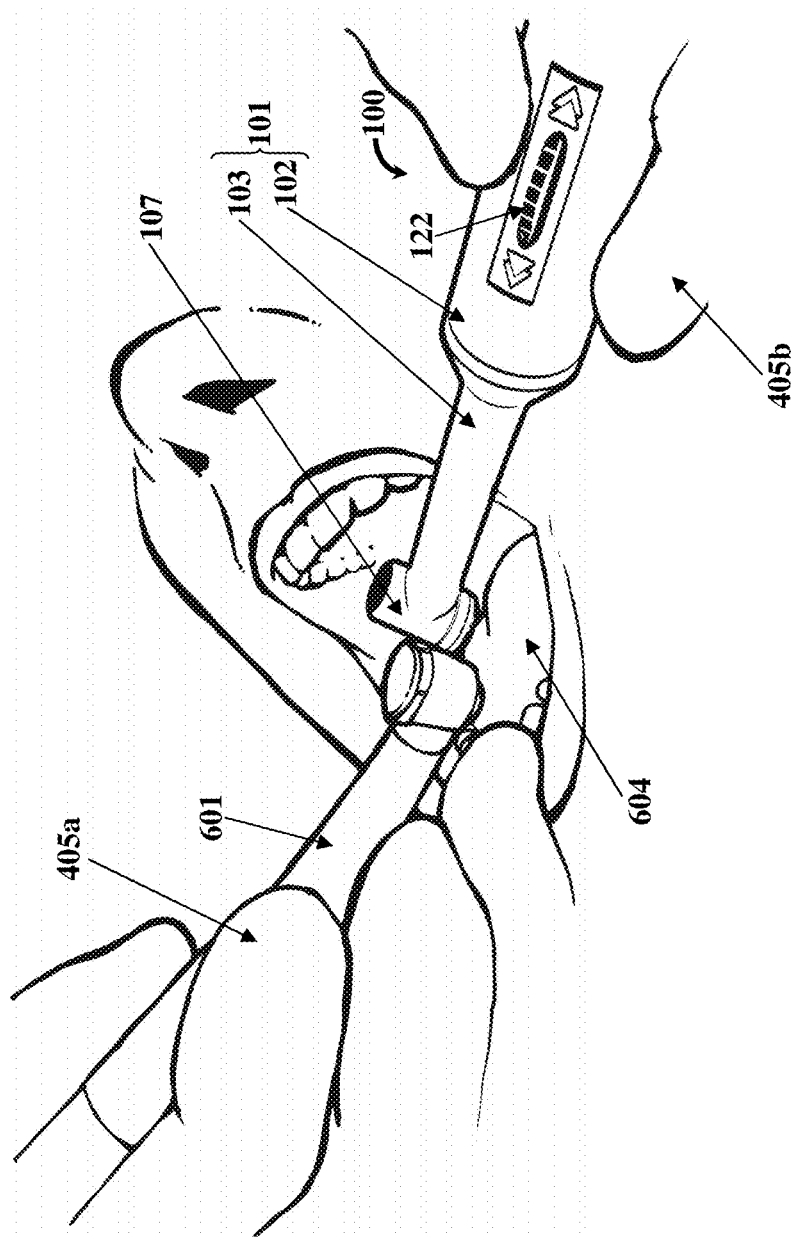
Figure 6E:
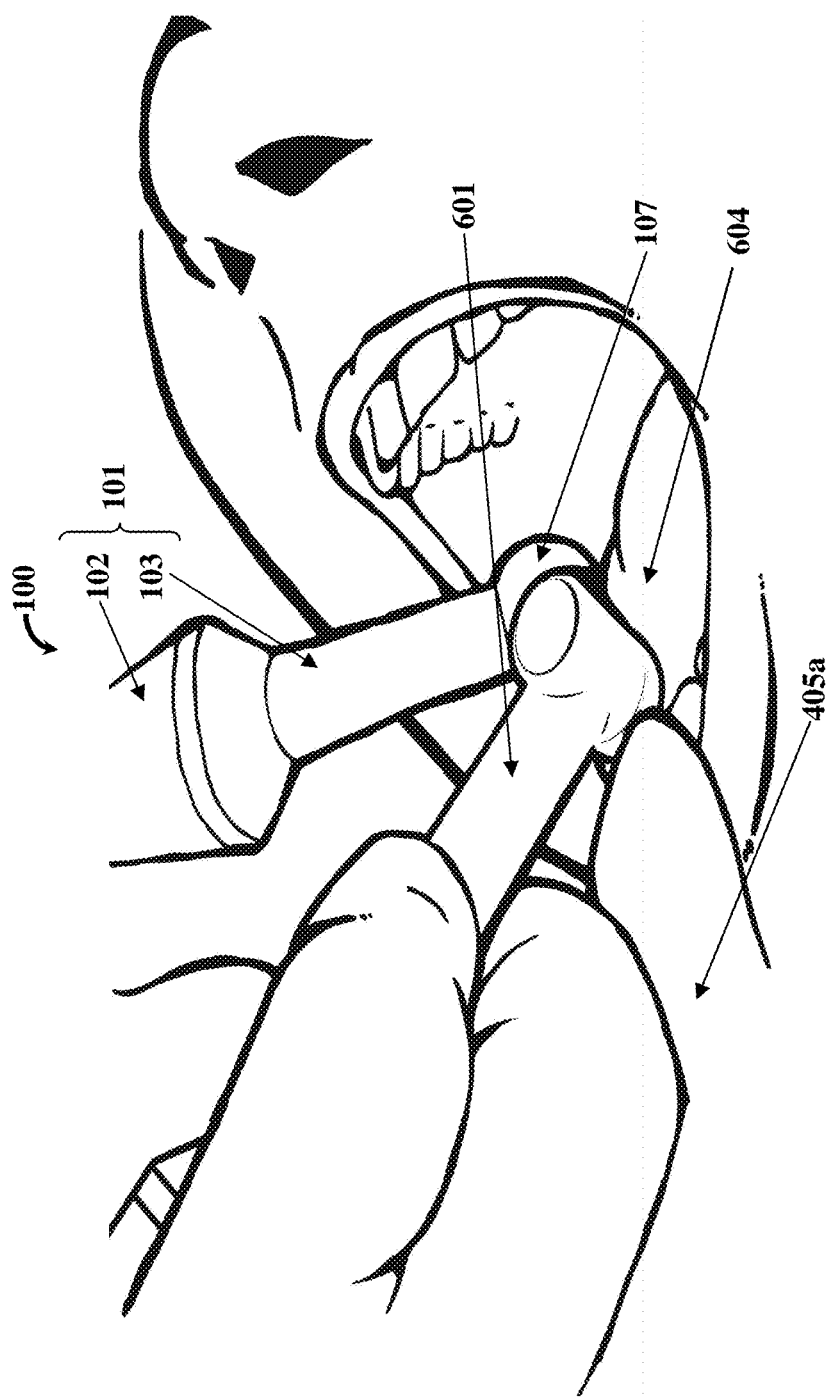

The visualization apparatus 100 creates a magnified image 502 exemplarily illustrated in FIG. 6B, of the operating field 604 and transmits the magnified image 502 to the processor 116 of the visualization apparatus 100 via the image receiver 115 as disclosed in the detailed description of FIGS. 1A-1B. The processor 116 renders the magnified image 502 to the viewer 401 as exemplarily illustrated in FIG. 6B. The magnified image 502 can also be displayed on other viewers 401, for example, a monitor that can be set up in front of the user 405 to show the magnified image 502. However, the user 405 will have to turn his/her head to see the monitor. Since the wearable viewer 401 provides a view of the magnified image 502 over a glass frame, the user 405 can perform the medical procedure without bending or turning his/her head. Displaying the magnified image 502 on the wearable viewer 401 ensures that the user 405 performing the medical procedure views the operating field 604 with minimal effort and hence minimizes the probability of strain on the eye and the neck of the user 405. The wearable viewer 401 can be worn as an eye glass providing both digital images and direct vision.

The visualization apparatus 100 renders the magnified image 502 to the wearable viewer 401 in an orientation which is a direct vision of the operating field 604. Therefore, when the user 405 turns his/her head, the visualization apparatus 100 adjusts the vision or the orientation of the operating field 604 and provides the magnified image 502 to the wearable viewer 401 in an orientation substantially similar to the operating field 604. The orientation of the magnified image 502 aligns with the orientation of the direction of vision and does not change with the orientation of the visualization apparatus 100. As the user's 405 hand 405b moves in the same direction as the magnified image 502 rendered by the visualization apparatus 100, the wearable viewer 401 requires minimal training and adaptation. In an embodiment, the visualization apparatus 100 displays an orientation marking arrow 602 in a viewing window of the wearable viewer 401 as exemplarily illustrated in FIG. 6B. The visualization apparatus 100 also provides a viewing ruler 603 to gauge the relative size of the operating field 604 as exemplarily illustrated in FIG. 6B.

The visualization apparatus 100 is operably coupled to one or more command sensors 403a, 403b, etc., for example, microphones as disclosed in the detailed description of FIGS. 4A-4B. In an embodiment, when the user 405 uses the wearable viewer 401, the visualization apparatus 100 is operably connected to the command sensors 403a, 403b, etc., provided by the wearable viewer 401 for receiving audio or voice signals. The command sensors 403a, 403b, etc., or the microphones of the wearable viewer 401 detects, for example, voice signals from the user 405 and transmits the voice signals to the control system 402 operably connected to the wearable viewer 401 as exemplarily illustrated in FIGS. 4A-4B. In this example, the control system 402 is incorporated in the wearable viewer 401. The voice activated command software 402a recognizes user commands from the voice signals and convert the user commands into executable commands by a method similar to the operation of, for example, the iPhone® of Apple, Inc., in which the voice signals are recognized by software applications inside the iPhone®. In an example, to adjust the focus of the visualization apparatus 100, without the involvement of the user's 405 hand 405b or the user's 405 foot, the command sensors 403a, 403b, etc., or the microphones of the wearable viewer 401 convert the voice signals into electrical signals, which enable the voice activated command software 402a to transmit instructions to the processor 116 of the visualization apparatus 100 for adjusting the focus of the visualization apparatus 100. The command sensors 403a, 403b, etc., or the microphones of the wearable viewer 401 in operative communication with the voice activated command software 402a limit voice control to the user 405 only. Since the visualization apparatus 100 disclosed herein is configured for use in dental and medical fields, the method and system 400 disclosed herein provide the voice activated command software 402a to bridge or connect with the applications in the wearable viewer 401.

Figure 7:
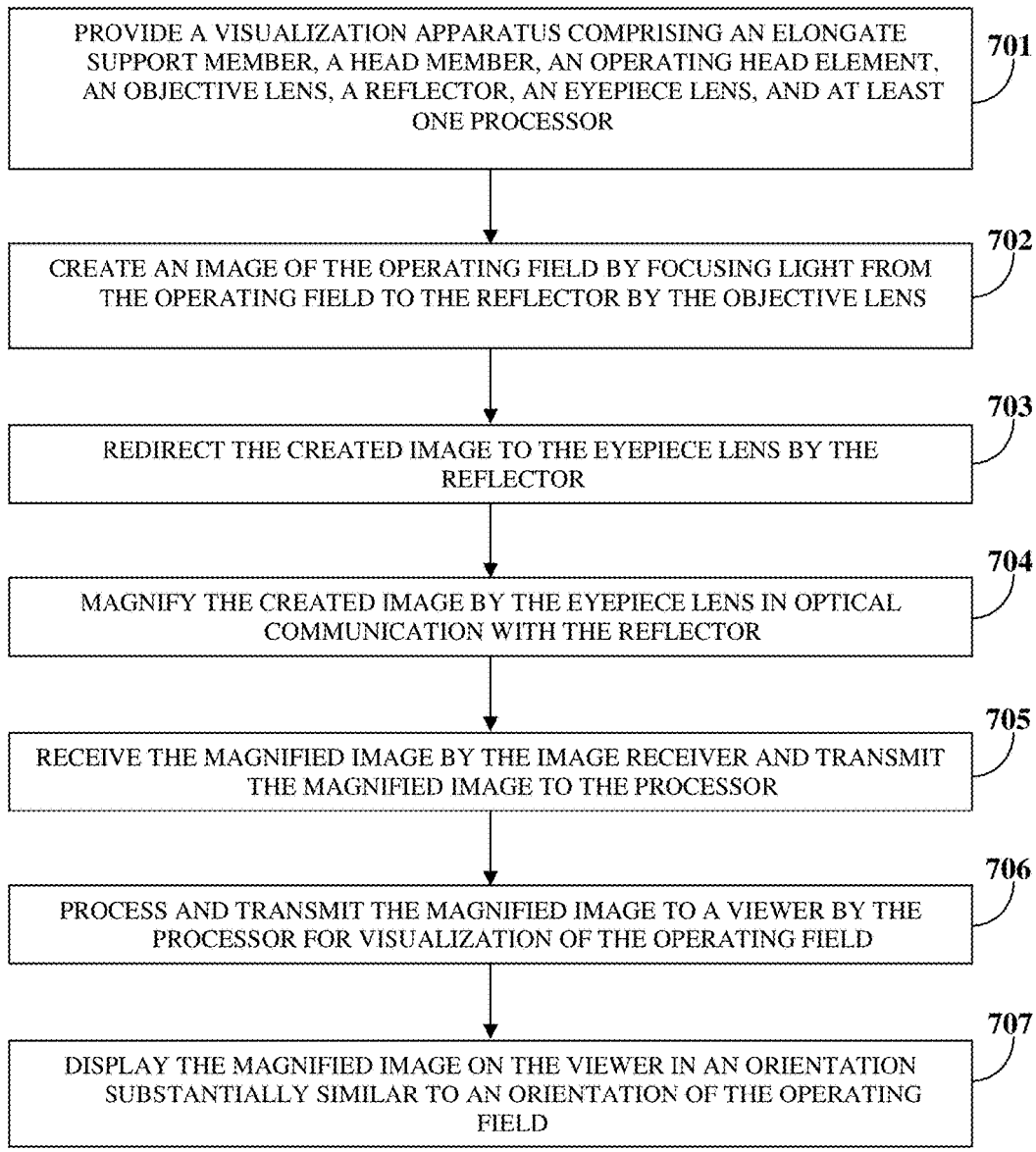
FIG. 7 illustrates a method for enhancing hand-eye coordination during a medical procedure.

FIG. 7 illustrates a method for enhancing hand-eye coordination during a medical procedure. The method disclosed herein provides 701 the visualization apparatus 100 exemplarily illustrated in FIGS. 1A-1B, FIGS. 2A-2D, and FIG. 3 for capturing an image of an operating field 604 exemplarily illustrated in FIGS. 6D-6E during the medical procedure. The visualization apparatus 100 comprises the elongate support member 101, the head member 107, the operating head element 109, and the processor 116 as disclosed in the detailed description of FIGS. 1A-1B. The objective lens 111 exemplarily illustrated in FIG. 1A, of the visualization apparatus 100 creates 702 an image of the operating field 604, during the medical procedure by focusing light from the operating field 604 to the reflector 113 exemplarily illustrated in FIGS. 1A-1B. The reflector 113 of the visualization apparatus 100 redirects 703 the created image to the eyepiece lens 114 exemplarily illustrated in FIGS. 1A-1B. The eyepiece lens 114 in optical communication with the reflector 113 magnifies 704 the created image. The image receiver 115 receives 705 the magnified image 502 exemplarily illustrated in FIGS. 5A-5B and transmits 705 the magnified image 502 to the processor 116 of the visualization apparatus 100. The processor 116 processes and transmits 706 the magnified image 502 to the viewer 401 exemplarily illustrated in FIGS. 4A-4B and FIG. 6A, for visualization of the operating field 604 during the medical procedure. The viewer 401 displays 707 the magnified image 502 in an orientation substantially similar to the orientation of the operating field 604, thereby enhancing the hand-eye coordination during the medical procedure. The light sources 117 exemplarily illustrated in FIGS. 1A-1B illuminate the operating field 604 during the medical procedure.

The method disclosed herein further provides the control system 402 exemplarily illustrated in FIGS. 4A-4B, operably connected to the viewer 401 and the visualization apparatus 100. The command sensors 403a, 403b, etc., exemplarily illustrated in FIGS. 4A-4B, detect user commands, for example, audio commands, voice commands, textual commands, video commands, etc., provided by the user 405 in one or more modes, for example, an audio mode, a video mode, a text mode, an audiovisual mode, a multimedia mode, etc., and any combination thereof, and transmit the user commands to the control system 402. The processor 402b of the control system 402 processes the transmitted user commands for transmitting instructions to the visualization apparatus 100 for performing actions, for example, adjusting a position of the eyepiece lens 114 of the visualization apparatus 100 for adjusting focus of the objective lens 111 of the visualization apparatus 100, changing the orientation of the magnified image 502 for enhanced visualization of the operating field 604, etc.

Many medical offices or dental offices are equipped with computers in each operating room. In an embodiment, the computers comprise the viewer 401 and the control system 402. In this embodiment, the control system 402 is in operative communication with the voice activated command software 402a installed in the computers. The user 405 exemplarily illustrated in FIGS. 4A-4B and FIG. 6A, can train the voice activated command software 402a to recognize certain words as user commands. The voice activated command software 402a requests a confirmation message from the user 405 before executing each user command via the processor 402b, by repeating the user command and requesting the user 405 to reply with a "yes" message when the interpretation is correct and a "no" message when the interpretation incorrect. The voice activated command software 402a is trained to recognize certain words pronounced by the user 405, for example, yes, no, focus in, focus out, etc. For example, when the user 405 wants to change the focus of the visualization apparatus 100, the user 405 says "focus in". The voice activated command software 402a recognizes the user command "focus in" and requests the user 405 to confirm with a "yes" message or a "no" message. When the user 405 confirms the words or the user command, the voice activated command software 402a defines instructions for execution of the user command and transmits the instructions to the processor 402b of the control system 402. The processor 402b processes the user command and transmits instructions to the processor 116 of the visualization apparatus 100 to proceed with the adjustment of the focus by an incremental step.

In an embodiment, the method disclosed herein further provides the image recognition application 401b for recognizing the orientation of the magnified image 502 captured by the visualization apparatus 100. The image recognition application 401b corrects the orientation of the magnified image 502 to match the orientation of the operating field 604. In another embodiment, the method disclosed herein further provides the orientation indicator 121 embedded in the elongate support member 101 or the head member 107. The orientation indicator 121 is operably connected to the viewer 401. The orientation indicator 121 corrects the orientation of the magnified image 502 to a preset orientation as disclosed in the detailed description of FIGS. 1A-1B.

Consider an example where a dentist is performing a dental procedure, for example, a root canal treatment on a patient using the visualization apparatus 100 disclosed herein. The magnified image 502 of the pulpal chamber of the tooth from the visualization apparatus 100 is transmitted through the eyepiece lens 114 of the visualization apparatus 100 into the image receiver 115 within the visualization apparatus 100. The processor 116 of the visualization apparatus 100 operably connected to the image receiver 115 transmits the magnified image 502, for example, through a universal serial bus (USB) chord into the control system 402 of the wearable viewer 401. The processor 116 may also transmit the magnified image 502 to an external control system 402 present in the dentist's office. The control system 402 analyzes the magnified image 502 data using a software application installed in the control system 402 and displays the magnified image 502 on the viewing media, namely, the wearable viewer 401 directly or via a network 404. The visualization apparatus 100 displays the images on the wearable viewer 401 at any head position of the dentist, and hence the dentist does not have to turn his/her head away from his/her surgical activity during the root canal treatment. When the dentist wants to adjust the focus of the visualization apparatus 100, he/she instructs the visualization apparatus 100 to adjust the focus by using user commands or voice signals through the microphones or command sensors 403a, 403b, etc., of the wearable viewer 401. The control system 402 operably connected to the command sensors 403a, 403b, etc., processes the voice signals and transmits instructions to the visualization apparatus 100 for adjusting the focus. The visualization apparatus 100, on receiving the instructions, automatically adjusts the focus of the pulpal chamber of the tooth as per the dentist's requirements. Other actions besides focusing can also be performed in a similar method. Thus, the visualization apparatus 100 disclosed herein provides the magnified image 502 of the pulpal chamber of the tooth directly to the eyes of the dentist and enhances hand-eye coordination during the dental procedure.

It will be readily apparent that the various methods, algorithms, and computer programs disclosed herein may be implemented on computer readable media appropriately programmed for general purpose computers and computing devices. As used herein, the term "computer readable media" refers to non-transitory computer readable media that participate in providing data, for example, instructions that may be read by a computer, a processor or a similar device. Non-transitory computer readable media comprise all computer readable media, for example, non-volatile media, volatile media, and transmission media, except for a transitory, propagating signal. Non-volatile media comprise, for example, optical discs or magnetic disks and other persistent memory volatile media including a dynamic random access memory (DRAM), which typically constitutes a main memory. Volatile media comprise, for example, a register memory, a processor cache, a random access memory (RAM), etc. Transmission media comprise, for example, coaxial cables, copper wire, fiber optic cables, modems, etc., including wires that constitute a system bus coupled to a processor, etc. Common forms of computer readable media comprise, for example, a floppy disk, a flexible disk, a hard disk, magnetic tape, a laser disc, a Blu-ray Disc®, any magnetic medium, a compact disc-read only memory (CD-ROM), a digital versatile disc (DVD), any optical medium, a flash memory card, punch cards, paper tape, any other physical medium with patterns of holes, a random access memory (RAM), a programmable read only memory (PROM), an erasable programmable read only memory (EPROM), an electrically erasable programmable read only memory (EEPROM), a flash memory, any other memory chip or cartridge, or any other medium from which a computer can read.

The computer programs that implement the methods and algorithms disclosed herein may be stored and transmitted using a variety of media, for example, the computer readable media in a number of manners. In an embodiment, hardwired circuitry or custom hardware may be used in place of, or in combination with, software instructions for implementation of the processes of various embodiments. Therefore, the embodiments are not limited to any specific combination of hardware and software. In general, the computer program codes comprising computer executable instructions may be implemented in any programming language. Some examples of programming languages that can be used comprise C, C++, C#, Java®, JavaScript®, Fortran, Ruby, Pascal, Perl®, Python®, Visual Basic®, MATLAB®, etc. Other object-oriented, functional, scripting, and/or logical programming languages may also be used. The computer program codes or software programs may be stored on or in one or more mediums as object code. Various aspects of the method and system disclosed herein may be implemented as programmed elements, or non-programmed elements, or any suitable combination thereof.

The present invention can be configured to work in a network environment comprising one or more computers that are in communication with one or more devices via a network. The computers may communicate with the devices directly or indirectly, via a wired medium or a wireless medium such as the Internet, a local area network (LAN), a wide area network (WAN) or the Ethernet, a token ring, or via any appropriate communications mediums or combination of communications mediums. Each of the devices may comprise processors, for example, the Intel® processors, Advanced Micro Devices (AMD®) processors, UltraSPARC® processors, Hp® processors, International Business Machines (IBM®) processors, RISC based computer processors of ARM Holdings, Motorola® processors, etc., that are adapted to communicate with the computers. In an embodiment, each of the computers is equipped with a network communication device, for example, a network interface card, a modem, or other network connection device suitable for connecting to a network. Each of the computers and the devices executes an operating system, for example, the Linux® operating system, the Unix® operating system, any version of the Microsoft® Windows® operating system, the Mac OS of Apple Inc., the IBM® OS/2, the Palm OS®, the Android® OS, the Blackberry® OS, the Solaris operating system developed by Sun Microsystems, Inc., or any other operating system. Handheld devices execute operating systems, for example, the Android operating system, the Windows Phone™ operating system of Microsoft Corporation, the BlackBerry® operating system of Research in Motion Limited, the iOS operating system of Apple Inc., the Symbian® operating system of Symbian Foundation Limited, etc. While the operating system may differ depending on the type of computer, the operating system will continue to provide the appropriate communications protocols to establish communication links with the network. Any number and type of machines may be in communication with the computers.

The present invention is not limited to a particular computer system platform, processor, operating system, or network. One or more aspects of the present invention may be distributed among one or more computer systems, for example, servers configured to provide one or more services to one or more client computers, or to perform a complete task in a distributed system. For example, one or more aspects of the present invention may be performed on a client-server system that comprises components distributed among one or more server systems that perform multiple functions according to various embodiments. These components comprise, for example, executable, intermediate, or interpreted code, which communicate over a network using a communication protocol. The present invention is not limited to be executable on any particular system or group of systems, and is not limited to any particular distributed architecture, network, or communication protocol.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials, and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may affect numerous modifications thereto and changes may be made without departing from the scope and spirit of the invention in its aspects.

We claim:

1. A visualization apparatus for enhancing hand-eye coordination during a medical procedure, comprising:
   an elongate support member configured to allow maneuvering of said visualization apparatus within an operating field;
   a head member operably connected to an upper end of said elongate support member at a predetermined angle with respect to said elongate support member, said head member at said predetermined angle configured to enhance accessibility to said operating field and motion control of said visualization apparatus within said operating field during said medical procedure;
   a reflector mounted along an inner surface of an angled wall of the head member;
   an operating head element operably connected to an upper end of said head member;
   an objective lens mounted on said operating head element, wherein said objective lens is in optical communication with said reflector, and wherein said objective lens is configured to focus light from said operating field to said reflector optically aligned with a focal point of said objective lens to create an image of said operating field during said medical procedure;
   an eyepiece lens accommodated within one of said elongate support member and said head member, said eyepiece lens in optical communication with said reflector and said objective lens is configured to magnify said created image; and
   a processor operably positioned within an axial hollow space defined within said elongate support member, said processor in operative communication with an image receiver positioned within said axial hollow space and to said eyepiece lens for receiving said magnified image, wherein said processor is configured to process and transmit said magnified image to a viewer for visualization of said operating field during said medical procedure, and wherein an orientation of said magnified image on said viewer is substantially similar to an orientation of said operating field, thereby enhancing said hand-eye coordination during said medical procedure.

2. The visualization apparatus of claim 1, wherein said elongate support member comprises:
an elongate handle defining a first axial hollow space, said first axial hollow space configured to accommodate said image receiver and said processor; and
a neck element operably connected to and axially extending from an upper end of said elongate handle.

3. The visualization apparatus of claim 1, wherein said head member is configured to define a hollow space in fluid communication with said axial hollow space defined within said elongate support member, wherein said hollow space of said head member is configured to accommodate said eyepiece lens.

4. The visualization apparatus of claim 1, wherein said reflector is configured to redirect said created image to said eyepiece lens optically aligned with said focal point of said objective lens to enable said eyepiece lens to magnify said created image.

5. The visualization apparatus of claim 1, further comprising a plurality of light sources mounted proximal to and surrounding said objective lens on said operating head element, wherein said light sources are configured to illuminate said operating field during said medical procedure.

6. The visualization apparatus of claim 1, further comprising an adjustable member operably connected to a frame configured to support said eyepiece lens within said one of said elongate support member and said head member, wherein said adjustable member is configured to adjust a position of said eyepiece lens with respect to said objective lens for adjusting focus of said objective lens.

7. The visualization apparatus of claim 1, further comprising an adjustable member operably connected to a frame configured to support said image receiver within said axial hollow space of said elongate support member, wherein said adjustable member is configured to adjust a position of said image receiver with respect to said eyepiece lens for facilitating said reception of said magnified image by said image receiver.

8. The visualization apparatus of claim 1, further comprising an orientation indicator embedded in one of said elongate support member and said head member, wherein said orientation indicator is configured to record an instantaneous position and an instantaneous orientation of said visualization apparatus on said creation of said image of said operating field and transmit said recorded position and orientation of said visualization apparatus to said processor, and wherein said processor is further configured to correct said orientation of said magnified image based on said recorded position and orientation of said visualization apparatus to a preset orientation.

9. The visualization apparatus of claim 1, wherein said head member is rigidly connected to said upper end of said elongate support member at said predetermined angle with respect to said elongate support member.

10. The visualization apparatus of claim 1 being configured as a handpiece.

11. A system for enhancing hand-eye coordination during a medical procedure, comprising:
a visualization apparatus comprising:
an elongate support member configured to allow maneuvering of said visualization apparatus within an operating field;
a head member operably connected to an upper end of said elongate support member at a predetermined angle with respect to said elongate support member, said head member at said predetermined angle configured to enhance accessibility to said operating field and motion control of said visualization apparatus within said operating field during said medical procedure;
a reflector mounted along an inner surface of an angles wall of the head member;
an operating head element connected to an upper end of said head member;
an objective lens mounted on said operating head element, wherein said objective lens is in optical communication with said reflector, and wherein said objective lens is configured to focus light from said operating field to said reflector optically aligned with a focal point of said objective lens to create an image of said operating field during said medical procedure;
an eyepiece lens accommodated within one of said elongate support member and said head member, said eyepiece lens in optical communication with said reflector and said objective lens is configured to magnify said created image; and
a processor operably positioned within an axial hollow space defined within said elongate support member, said processor in operative communication with an image receiver positioned within said axial hollow space and to said eyepiece lens for receiving said magnified image, wherein said processor is configured to process and transmit said magnified image to a viewer for visualization of said operating field during said medical procedure; and
said viewer operably connected to said visualization apparatus and configured to display said magnified image on a graphical user interface provided by said viewer in an orientation substantially similar to an orientation of said operating field, thereby enhancing said hand-eye coordination during said medical procedure.

12. The system of claim 11, further comprising:
one or more command sensors operably connected to a control system, wherein said one or more command sensors are configured to detect user commands in one or more of a plurality of modes and transmit said user commands to said control system; and
said control system operably connected to said visualization apparatus, wherein said control system comprises a voice activated command software executable by a processor configured to process said transmitted user commands and transmit instructions to said visualization apparatus for performing one or more of a plurality of actions on said visualization apparatus.

13. The system of claim 12, wherein said actions comprise:
adjusting a position of said eyepiece lens of said visualization apparatus for adjusting focus of said objective lens of said visualization apparatus; and
changing said orientation of said magnified image for enhanced said visualization of said operating field.

14. The system of claim 11, further comprising an image recognition application installed in said viewer, said image recognition application executable by a processor configured to perform:
recognizing said orientation of said magnified image created by said visualization apparatus; and correcting said orientation of said magnified image to match said orientation of said operating field.

15. The system of claim 11, wherein said visualization apparatus further comprises an orientation indicator embedded in one of said elongate support member and said head member, wherein said orientation indicator is configured to record an instantaneous position and an instantaneous orientation of said visualization apparatus on said creation of said image of said operating field and transmit said recorded position and orientation of said visualization apparatus to said processor, and wherein said processor is further configured to correct said orientation of said magnified image based on said recorded position and orientation of said visualization apparatus to a preset orientation.

16. The system of claim 11, wherein said visualization apparatus further comprises a plurality of light sources mounted proximal to and surrounding said objective lens on said operating head element, wherein said light sources are configured to illuminate said operating field during said medical procedure.

17. The system of claim 11, wherein said visualization apparatus further comprises an adjustable member operably connected to a frame configured to support said eyepiece lens within said one of said elongate support member and said head member, wherein said adjustable member is configured to adjust a position of said eyepiece lens with respect to said objective lens for adjusting focus of said objective lens.

18. The system of claim 11, wherein said visualization apparatus further comprises an adjustable member operably connected to a frame configured to support said image receiver within said axial hollow space of said elongate support member, wherein said adjustable member is configured to adjust a position of said image receiver with respect to said eyepiece lens for facilitating said reception of said magnified image by said image receiver.

19. The system of claim 11, wherein said head member is rigidly connected to said upper end of said elongate support member at said predetermined angle with respect to said elongate support member.

* * * * *